United States Patent
Lee et al.

(10) Patent No.: US 10,781,488 B1
(45) Date of Patent: Sep. 22, 2020

(54) TEST KIT FOR DETECTING CONCENTRATION OF CARDIOVASCULAR DISEASE-RELATED BIOMARKER AND CONCENTRATION DETECTION METHOD FOR DETECTING CONCENTRATION OF CARDIOVASCULAR DISEASE-RELATED BIOMARKER

(71) Applicant: National Tsing Hua University, Hsinchu (TW)

(72) Inventors: Gwo-Bin Lee, Hsinchu (TW); Anirban Sinha, Hsinchu (TW); Priya Gopinathan, Hsinchu (TW); Yi-Da Chung, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 0 days.

(21) Appl. No.: 16/557,043

(22) Filed: Aug. 30, 2019

(30) Foreign Application Priority Data

Mar. 6, 2019 (TW) .............................. 108107497 A

(51) Int. Cl.
*C12N 15/115* (2010.01)
*C12Q 1/6876* (2018.01)

(52) U.S. Cl.
CPC .................................. *C12Q 1/6876* (2013.01)

(58) Field of Classification Search
None
See application file for complete search history.

*Primary Examiner* — J. E Angell

(57) ABSTRACT

The present disclosure relates to a test kit for detecting a concentration of a cardiovascular disease-related biomarker including a group selected from the group consisting of a first aptamer, a second aptamer and a third aptamer. The first aptamer has binding specificity to an N-terminal pro-brain natriuretic peptide (NT-proBNP). The second aptamer has binding specificity to a cardiac Troponin I (cTnI). The third aptamer has binding specificity to a fibrinogen.

12 Claims, 21 Drawing Sheets

Specification includes a Sequence Listing.

TEST KIT FOR DETECTING CONCENTRATION OF CARDIOVASCULAR DISEASE-RELATED BIOMARKER AND CONCENTRATION DETECTION METHOD FOR DETECTING CONCENTRATION OF CARDIOVASCULAR DISEASE-RELATED BIOMARKER

RELATED APPLICATIONS

This application claims priority to Taiwan Application Serial Number 108107497, filed Mar. 6, 2019, which is herein incorporated by reference.

SEQUENCE LISTING

The sequence listing submitted via EFS, in compliance with 37 CFR § 1.52(e)(5), is incorporated herein by reference. The sequence listing text file submitted via EFS contains the file "CP-4364-US_Sequence Listing", created on Aug. 28, 2019, which is 3,207 bytes in size.

BACKGROUND

Technical Field

The present disclosure relates to a test kit and a detection method thereof. More particularly, the present disclosure relates to a test kit for detecting a concentration of a cardiovascular disease-related biomarker including an aptamer that binds specifically to a cardiovascular disease-related biomarker and the concentration detection method thereof.

Description of Related Art

According to statistics released by the World Health Organization (WHO) in 2016, cardiovascular disease (CVD) is the topmost cause of deaths worldwide. Cardiovascular disease claims about 18 million lives each year, accounting for 31% of all deaths worldwide. There is a large amount of data suggesting the high risk of recurrence, morbidity, and mortality due to poor prognosis in cardiovascular disease, and many people are already at risk. While preventive measures are important, it is equally important to effectively predict the risk of cardiovascular disease and timely monitoring of the above for timely diagnosis and effective prognosis.

Conventional direct observations of cardiovascular disease can be achieved by performing an electrocardiogram, cardiac ultrasound, nuclear magnetic angiography or angiographic examination. However, the instruments mentioned above are installed in specific institutions, and it is not possible to conduct regular inspection and monitoring of all patients due to the limited availability of these medical resources. The more feasible method for detecting cardiovascular disease is conventional blood tests. However, using conventional indicators, such as low-density cholesterol, triglycerides, body mass index (BMI), waistline, blood pressure, and the presence of diabetes or abnormal renal function to determine the risks of cardiovascular disease has its importance but lacks in efficacy.

Therefore, we suggest the risk stratification of cardiovascular disease based upon detection of biomarkers in a biological specimen (serum or plasma) using a more convenient and cost-effective miniaturized rapid detection system using only a small amount of sample. A cheap device that can perform the test will help achieve a truly convenient, effective and economical cardiovascular disease risk assessment, achieving the goal of personalized medicine, which in turn can be effective in risk assessment and prognosis of cardiovascular disease.

Until now, antibodies have been used as the preferred affinity reagents as probes for the detection of biomarkers, regardless of the test reagent in biosensors. However, antibodies are costly to produce and have low stability at varied temperature range; they require stricter storage conditions and are limited by the target epitopes in many cases. The use of single-stranded DNA aptamer has many advantages, such as lower molecular weight and easier penetration through tissue, low chemical synthesis costs, established modification methods, and high stability, that make it suitable for therapeutic applications. Therefore, the development of suitable aptamers with high binding affinity for cardiovascular disease-related biomarkers can effectively help early detection of cardiovascular diseases and improve patient prognosis.

SUMMARY

According to one aspect of the present disclosure, a test kit for detecting a concentration of a cardiovascular disease-related biomarker includes a group selected from the group consisting of a first aptamer, a second aptamer and a third aptamer. The first aptamer has binding specificity to an N-terminal pro-brain natriuretic peptide (NT-proBNP) and includes a nucleotide sequence of SEQ ID NO: 1, the second aptamer has binding specificity to a cardiac Troponin I (cTnI) and includes a nucleotide sequence of SEQ ID NO: 2, and the third aptamer has binding specificity to a fibrinogen and includes a nucleotide sequence of SEQ ID NO: 3.

According to another aspect of the present disclosure, a concentration detection method for detecting a concentration of a cardiovascular disease-related biomarker in a sample includes steps as follows. The sample is provided. A binding step is performed, wherein the binding step is for mixing the sample with the test kit for detecting the concentration of the cardiovascular disease-related biomarker according to the aforementioned aspect and performing a binding reaction. A detecting step is performed, wherein the detecting step is for measuring a binding value of the sample and the test kit for detecting the concentration of the cardiovascular disease-related biomarker. A calculating step is performed, wherein the calculating step is for bringing the binding value into a regression equation established in advance to obtain the concentration of the cardiovascular disease-related biomarker in the sample.

BRIEF DESCRIPTION OF THE DRAWINGS

The present disclosure can be more fully understood by reading the following detailed description of the embodiment, with reference made to the accompanying drawings as follows.

DETAILED DESCRIPTION

Figure 1A:
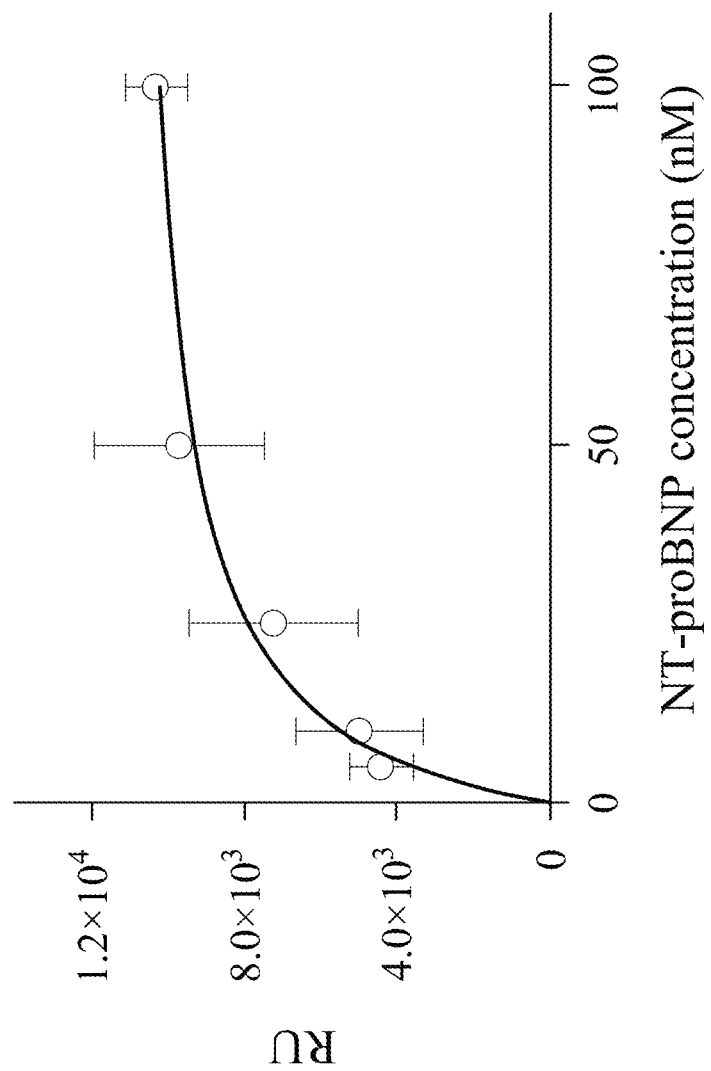
FIG. 1A shows a curve of binding affinity for one example of a first aptamer of the present disclosure.

A novel test kit for detecting a concentration of a cardiovascular disease-related biomarker is provided. The test kit for detecting the concentration of the cardiovascular disease-related biomarker of the present disclosure includes at least one aptamer having high binding specificity to a cardiovascular disease-related biomarker. A binding specificity of the at least one aptamer to the cardiovascular disease-related biomarker is analyzed by in vitro test for verifying that the test kit for detecting the concentration of the cardiovascular disease-related biomarker of the present disclosure is highly specific for the cardiovascular disease-related biomarker. Therefore, the test kit for detecting the concentration of the cardiovascular disease-related biomarker of the present disclosure can be used to assist in early detection of cardiovascular diseases.

The term "aptamer" is an oligonucleotide or peptide molecule that binds to a specific target molecule. The aptamer is usually created by selecting it from a large random sequence pool to screen the nucleic acid having binding specificity to the target molecule, and can be applied in the development of macromolecular drugs and clinical diagnostic studies. As used herein, "aptamer" refers to a nucleic acid aptamer that has been engineered through repeated rounds of in vitro selection or equivalently, SELEX (systematic evolution of ligands by exponential enrichment) to bind to various molecular targets such as small molecules, proteins, nucleic acids, cells, tissues and organisms.

The term "nucleotide" refers to a polymer form of nucleotides of any length including deoxyribonucleotides, ribonucleotides, and/or analogs or derivatives thereof. The nucleotide sequences shown in the present specification are arranged in the 5' to 3' direction.

The term "N-terminal pro-brain natriuretic peptide (NT-proBNP)" refers to a neurohormone. The study found that the ventricular myocytes secrete a 134-amino acid prohormone composite and then split into a pro-brain natriuretic peptide consisting of 108 amino acids. When entering the circulation, the pro-brain natriuretic peptide splits again into 76-amino acid NT-proBNP and 32-amino acid brain natriuretic peptide (BNP). When the left ventricle is dysfunctional, NT-proBNP is secreted to compensate for ventricular wall expansion and reduce the ventricular load. The concentration of the NT-ProBNP in the blood is increased proportionally to the degree of heart failure as per the New York Heart Association (NYHA), and the severity of heart failure can be determined by measuring the concentration of the NT-ProBNP in the blood. Therefore, the NT-proBNP is an important biochemical indicator of heart failure.

The term "cardiac Troponin I (cTnI)" refers to a subunit of the troponin complex, and the troponin complex is a heterologous protein that binds to thin filaments. The troponin complex plays an important regulatory role in skeletal muscle and myocardial contraction. The troponin complex includes three subunits: troponin T (TnT), troponin I (TnI), and troponin C (TnC). In humans, TnI has three subtypes, in which there are two subtypes of TnI (skTnI) in human skeletal muscle tissue, one expressed in slow skeletal muscle tissue and the other expressed in fast skeletal muscle tissue. The third subtype of TnI (cTnI) is myocardial, which is only present in cardiac tissue. When cardiomyocytes are damaged or die, intracellular cTnI is excreted from the cell and can be detected in the blood. When the concentration of the cTnI in the blood is greater than 0.04 ng/mL, acute myocardial infarction may be confirmed. Besides, the expression of the cTnI may continue to rise for up to 10 days after myocardial infarction, which can be used as a basis for the diagnosis of recent myocardial infarction or reinfarction, and can also be used to predict the extent of infarction and prognosis. Therefore, the cTnI can be used as an important biomarker for determining myocardial infarction.

The term "fibrinogen" belongs to the first coagulation factor, which is synthesized in the liver. The fibrinogen is cleaved by thrombin during blood coagulation to form fibrin, which binds to platelets to promote clot agglutination. After 24 hours of an inflammatory response, the body begins to secrete fibrinogen to promote agglutination of red blood cells. Besides, the expression of the fibrinogen in patients with arteriosclerosis is elevated. Therefore, the fibrinogen can be used as an indicator to assess the risk of inflammation and cardiovascular disease.

Reference will now be made in detail to the present embodiments of the present disclosure, examples of which are illustrated in the accompanying drawings.

I. Test Kit for Detecting the Concentration of the Cardiovascular Disease-Related Biomarker of the Present Disclosure The test kit for detecting the concentration of the cardiovascular disease-related biomarker of the present disclosure includes a group selected from the group consisting of a first aptamer, a second aptamer and a third aptamer. The first aptamer has binding specificity to the NT-proBNP, the second aptamer has binding specificity to the cTnI, and the third aptamer has binding specificity to the fibrinogen.

One example of the first aptamer of the present disclosure is N20a, which includes a nucleotide sequence of SEQ ID NO: 1. Another example of the first aptamer of the present disclosure is N10, which includes a nucleotide sequence of SEQ ID NO: 4. Still another example of the first aptamer of the present disclosure is N15, which includes a nucleotide sequence of SEQ ID NO: 5. Yet another example of the first aptamer of the present disclosure is N21a, which includes a nucleotide sequence of SEQ ID NO: 6.

One example of the second aptamer of the present disclosure is Tn2, which includes a nucleotide sequence of SEQ ID NO: 2. Another example of the second aptamer of the present disclosure is cTni3, which includes a nucleotide sequence of SEQ ID NO: 7. Still another example of the second aptamer of the present disclosure is cTni6, which includes a nucleotide sequence of SEQ ID NO: 8.

One example of the third aptamer of the present disclosure is F03s, which includes a nucleotide sequence of SEQ ID NO: 3. Another example of the third aptamer of the present disclosure is F17a, which includes a nucleotide sequence of SEQ ID NO: 9. Still another example of the third aptamer of the present disclosure is F13a, which includes a nucleotide sequence of SEQ ID NO: 10. Yet another example of the third aptamer of the present disclosure is F37a, which includes a nucleotide sequence of SEQ ID NO: 11.

The first aptamer, the second aptamer and the third aptamer of the present disclosure can be prepared using conventional methods known in the art. The first aptamer, the second aptamer and the third aptamer of the present disclosure can be in a linear or cyclic form, and can be RNA, DNA (for example, single-stranded DNA), modified nucleic acid, or a mixture thereof. The first aptamer, the second aptamer, and the third aptamer can be non-natural molecules (for example, containing a nucleotide sequence that is not found in the native gene or containing modified nucleotides that are not found in nature). Alternatively, the first aptamer, the second aptamer, and the third aptamer can contain a nucleotide sequence that does not encode a functional peptide.

Also, the test kit for detecting the concentration of the cardiovascular disease-related biomarker can further include a first detectable label, a second detectable label and/or a third detectable label. The first detectable label is bound on the first aptamer, wherein the first detectable label can be selected from the group consisting of a radioisotope, an enzyme, a fluorescent tag, a chemiluminescent tag, and a magnetic substance. The second detectable label is bound on the second aptamer, wherein the second detectable label can be selected from the group consisting of the radioisotope, the enzyme, the fluorescent tag, the chemiluminescent tag, and the magnetic substance. The third detectable label is bound on the third aptamer, wherein the third detectable label can be selected from the group consisting of the radioisotope, the enzyme, the fluorescent tag, the chemiluminescent tag, and the magnetic substance.

Example 1.1. Binding Affinity Test

Firstly, the binding affinities of the first aptamer, the second aptamer, and the third aptamer contained in the test kit for detecting the concentration of the cardiovascular disease-related biomarker of the present disclosure are tested. The surface plasmon resonance (SPR) method is used in the binding affinity test to measure the signal changes and calculate the dissociation constant (Kd) of the first aptamer, the second aptamer and the third aptamer against their respective target proteins. Alternatively, a primary antibody against the target protein and secondary antibody conjugated with an enzyme is used in test. The binding affinities of the first aptamer, the second aptamer, and the third aptamer against their respective target proteins are measured by detecting the intensities of luminescence.

Figure 1B:
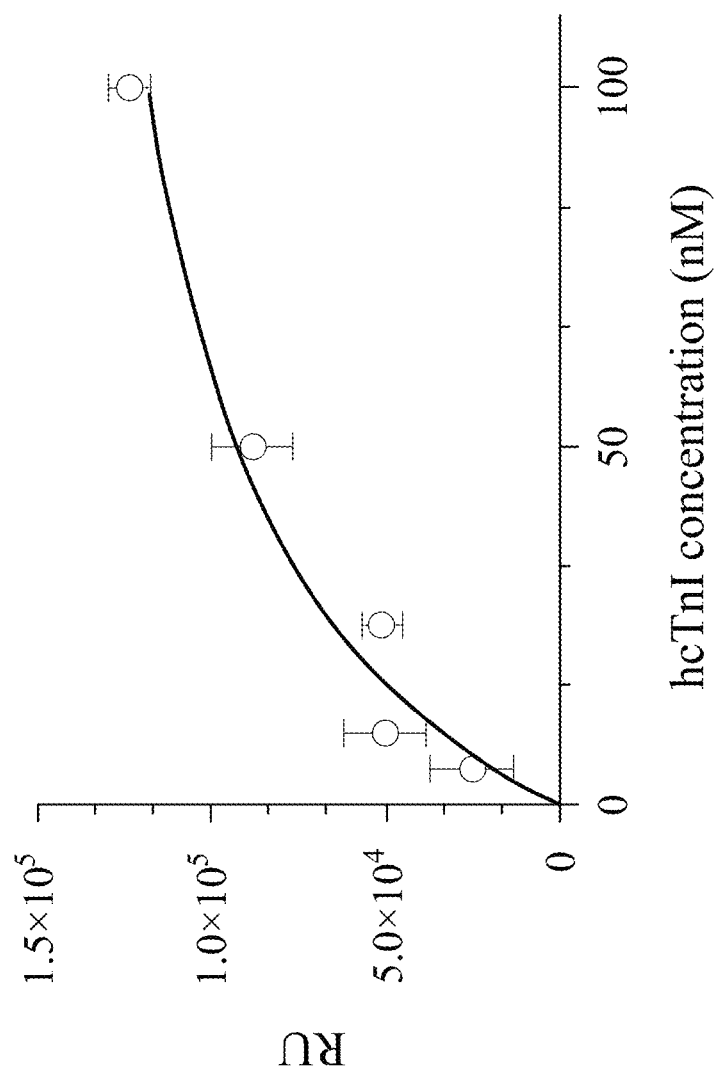
FIG. 1B shows a curve of binding affinity for one example of a second aptamer of the present disclosure.
Figure 1C:
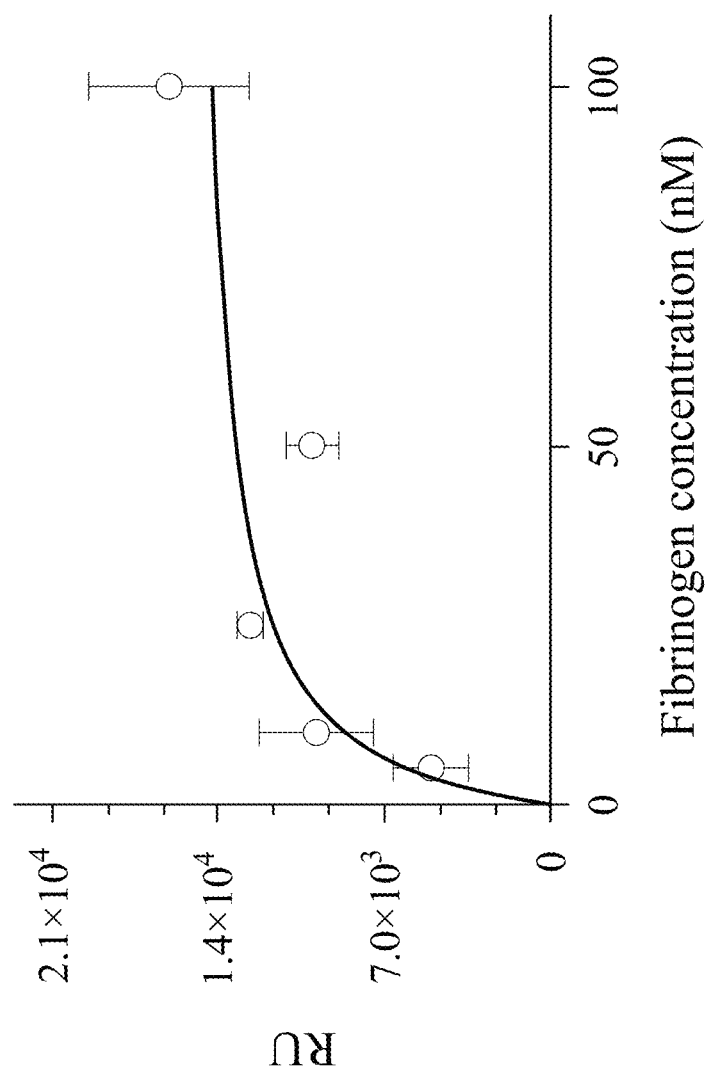
FIG. 1C shows a curve of binding affinity for one example of a third aptamer of the present disclosure.

Please refer to FIGS. 1A, 1B and 1C, which are curves of binding affinity for the first aptamer, the second aptamer and the third aptamer with their respective target proteins. The curves of binding affinity curve are obtained by plotting relative units (RU) of the first aptamer, the second aptamer or the third aptamer binding to its target protein and then detected by the surface plasmon resonance. FIG. 1A shows a curve of binding affinity for the first aptamer N20a against NT-proBNP, FIG. 1B shows a curve of binding affinity for the second aptamer Tn2 against hcTnI, and FIG. 1C shows a curve of binding affinity for the third aptamer F03s against fibrinogen.

In FIG. 1A, the first aptamer N20a has a high affinity with NT-proBNP, and the corresponding Kd value of the first aptamer N20a is 2.89 nM for NT-proBNP. In FIG. 1B, the second aptamer Tn2 has a high affinity with hcTnI, and the corresponding Kd value of the second aptamer Tn2 is 19.8 nM for hcTnI. In FIG. 1C, the third aptamer F03s has a high affinity with fibrinogen, and the corresponding Kd value of the third aptamer F03s is 4.4 nM for fibrinogen.

Figure 2A:
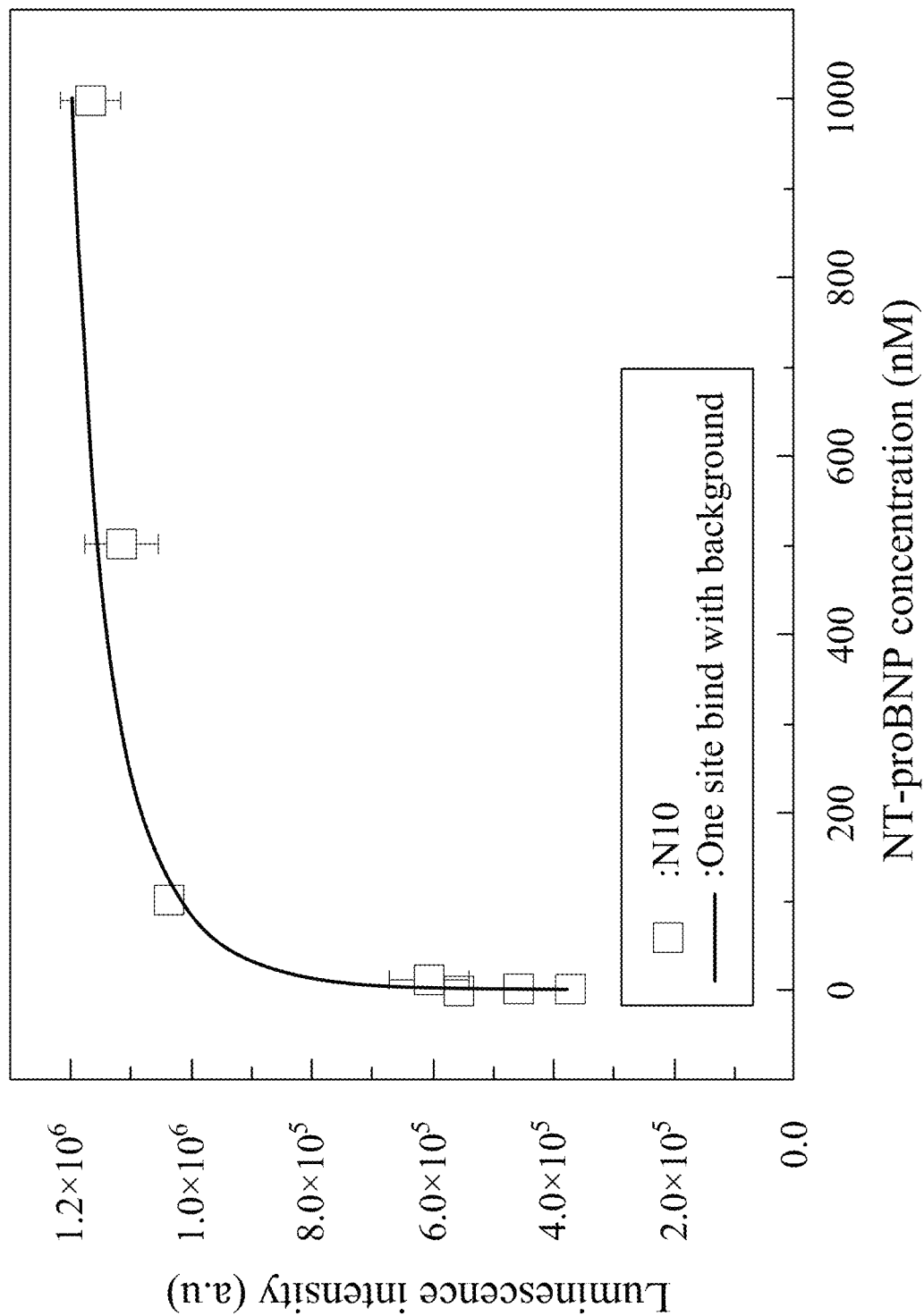
FIG. 2A is a curve of binding affinity for another example of a first aptamer of the present disclosure.
Figure 2B:
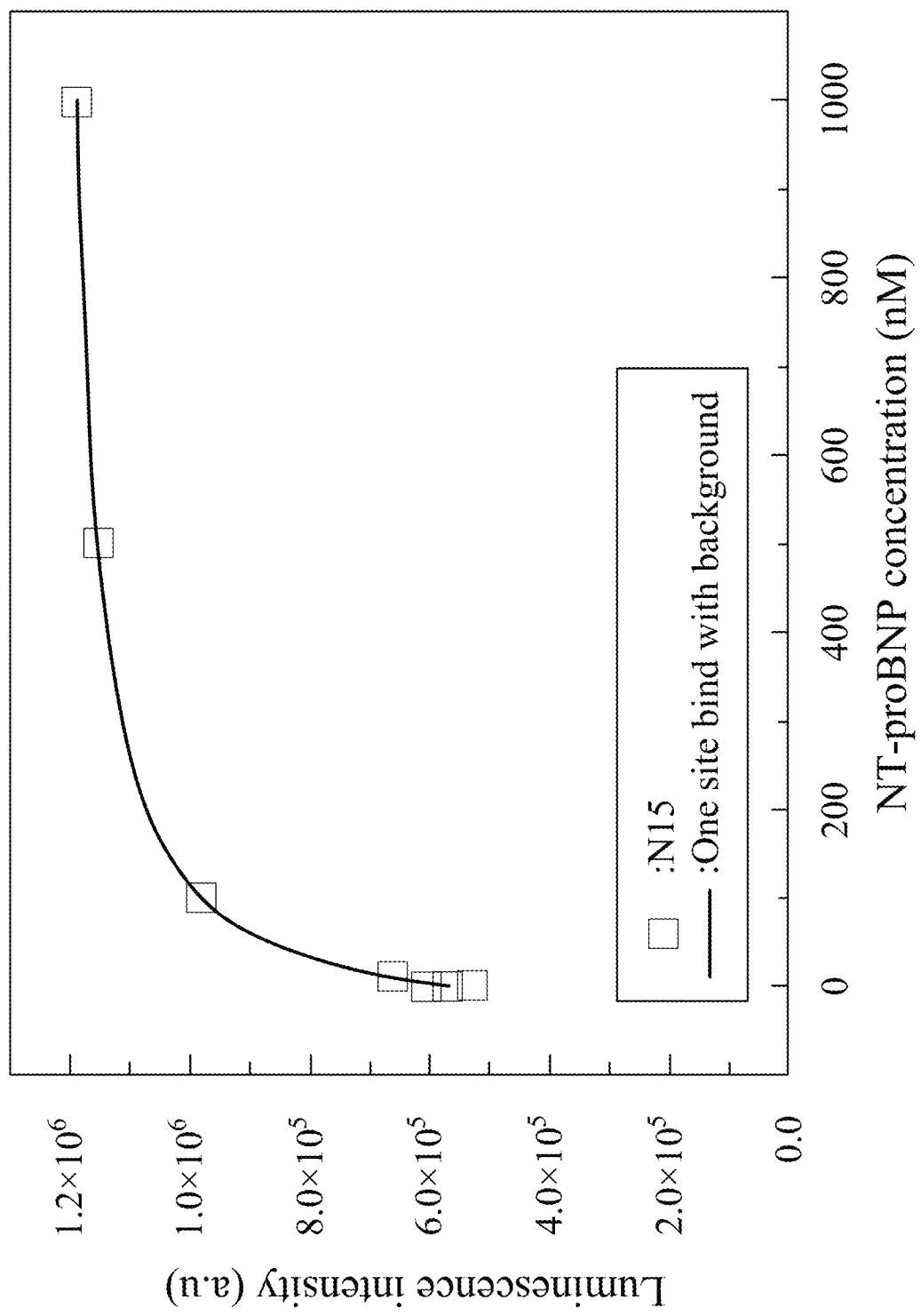
FIG. 2B is a curve of binding affinity for still another example of a first aptamer of the present disclosure.
Figure 2C:
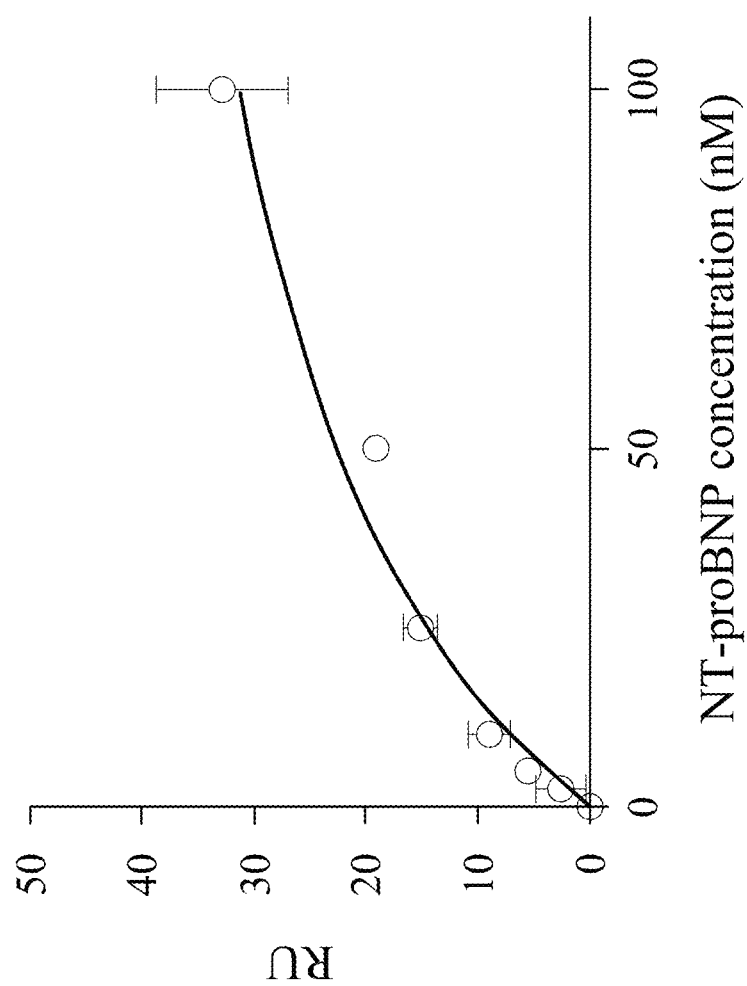
FIG. 2C is a curve of binding affinity for yet another example of a first aptamer of the present disclosure.
Figure 3A:
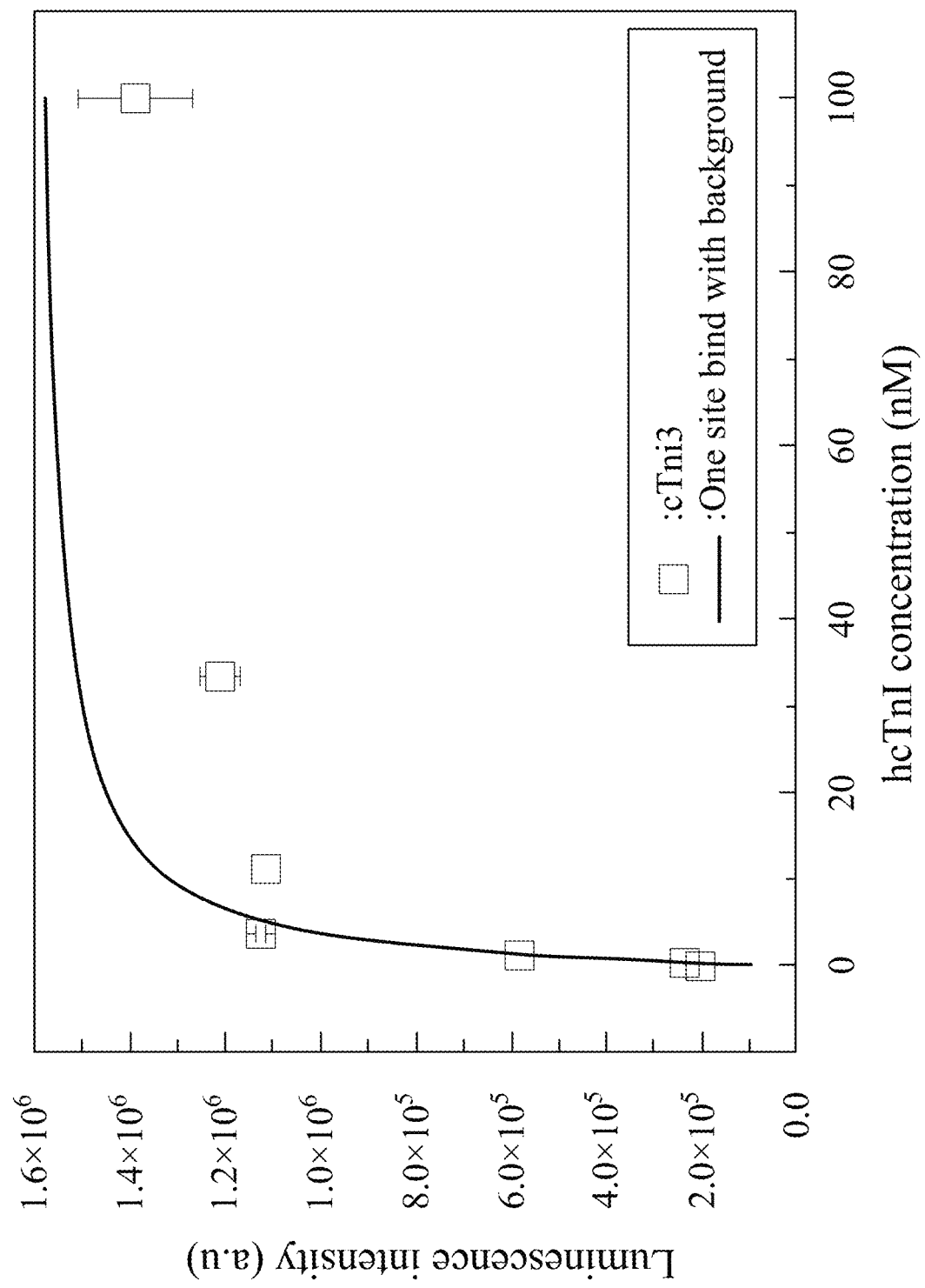
FIG. 3A is a curve of binding affinity for another example of a second aptamer of the present disclosure.
Figure 3B:
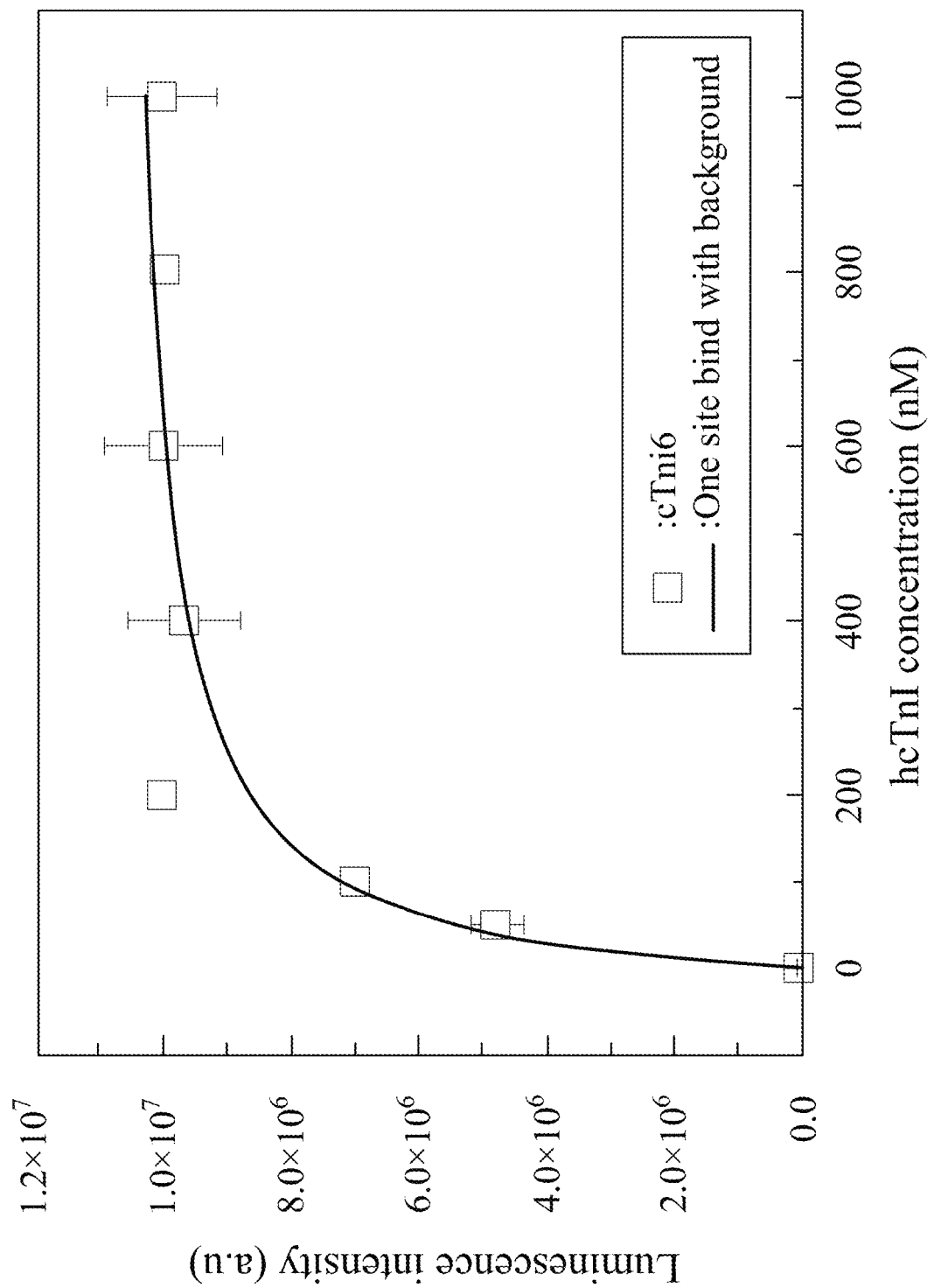
FIG. 3B is a curve of binding affinity for still another example of a second aptamer of the present disclosure.
Figure 4A:
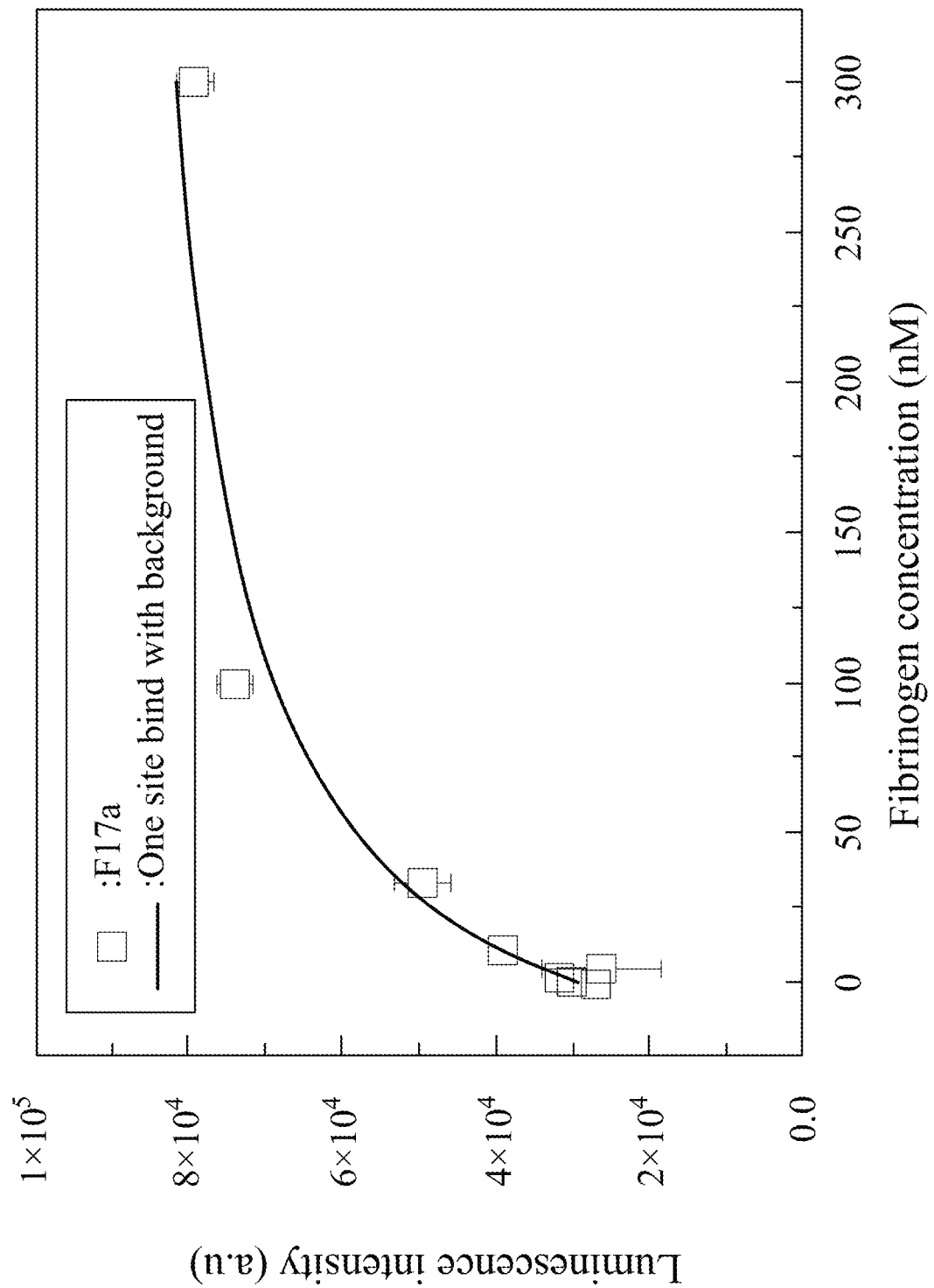
FIG. 4A is a curve of binding affinity for another example of a third aptamer of the present disclosure.
Figure 4B:
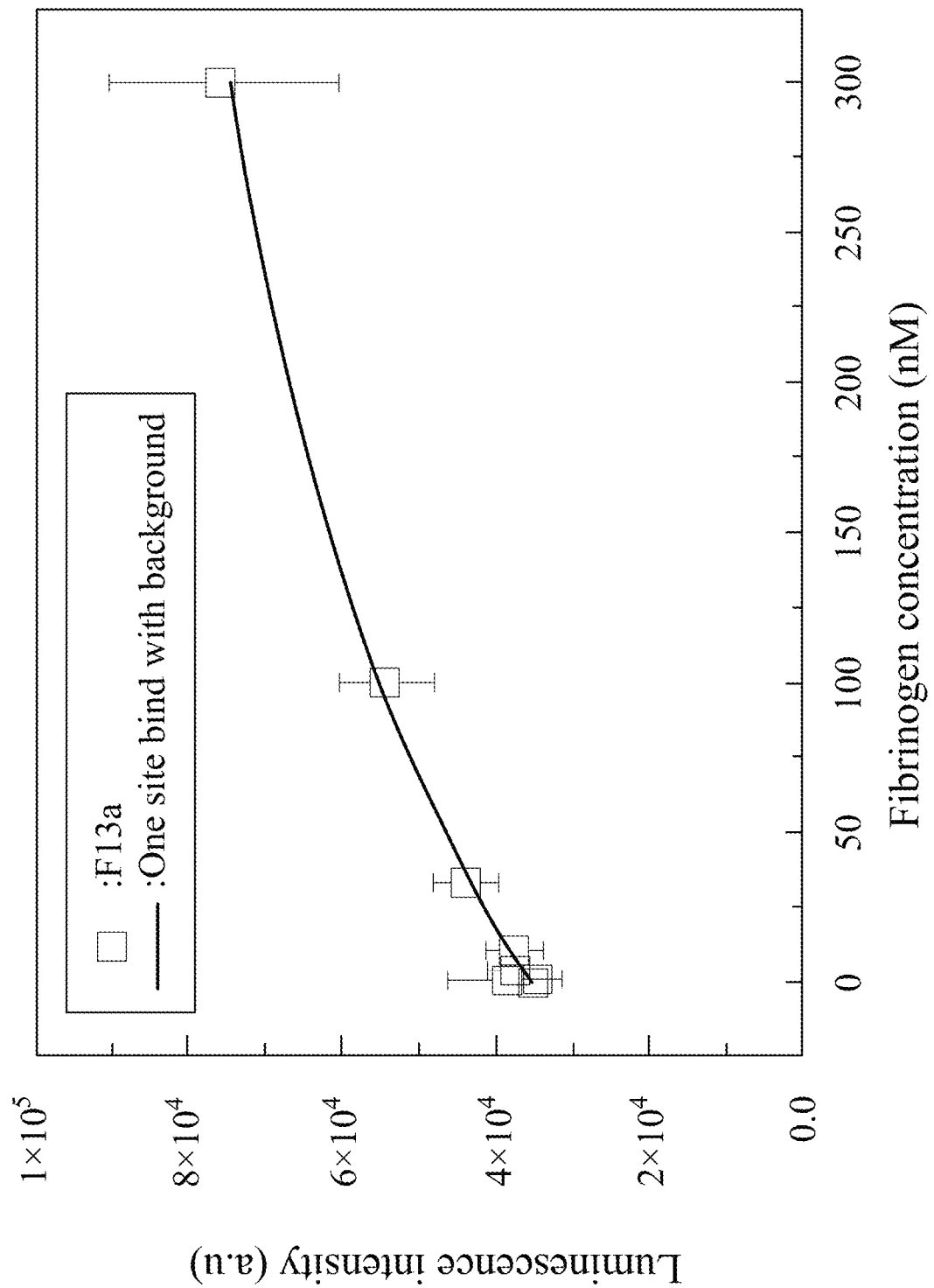
FIG. 4B is a curve of binding affinity for still another example of a third aptamer of the present disclosure.
Figure 4C:
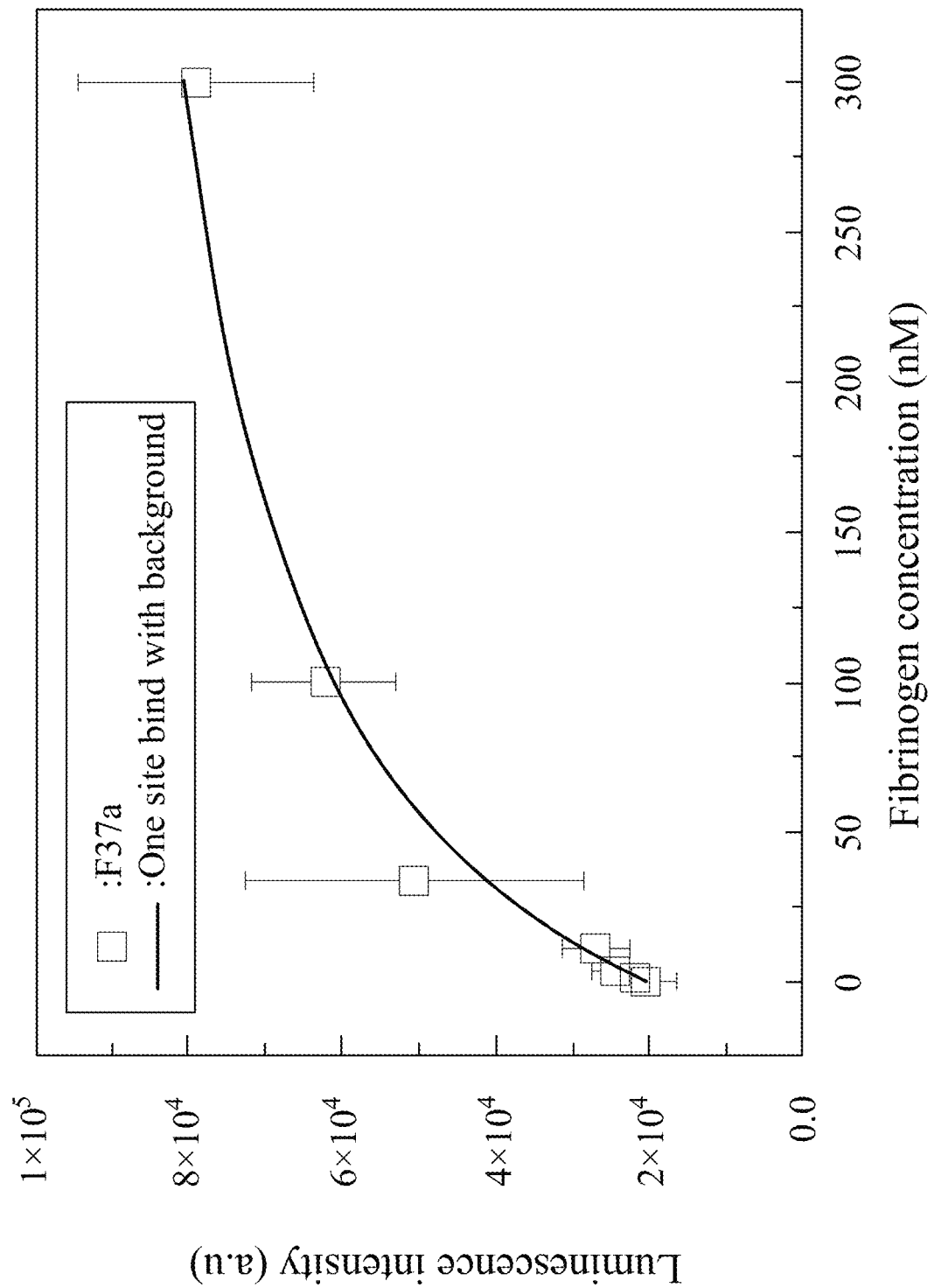
FIG. 4C is a curve of binding affinity for yet another example of a third aptamer of the present disclosure.

Please refer to FIGS. 2A, 2B, 3A, 3B, 4A, 4B and 4C, which are binding affinity curves for the first aptamer, the second aptamer and the third aptamer with their respective target proteins. The curves of binding affinity curve are plotted with luminescence intensity of the first aptamer, the second aptamer or the third aptamer with its target protein. The first aptamer, the second aptamer or the third aptamer is bound to the target protein. And then the aptamer-protein complex is incubated with antibodies against target proteins and further with secondary antibodies conjugated with the enzyme, which could produce luminescence when providing substrates. The signal of luminescence of the first aptamer, the second aptamer or the third aptamer is detected. FIG. 2A is a curve of binding affinity for the first aptamer N10 against NT-proBNP, and FIG. 2B is a curve of binding affinity for the first aptamer N15 against NT-proBNP. FIG. 3A is a curve of binding affinity for the second aptamer cTni3 against hcTnI, and FIG. 3B is a curve of binding affinity for the second aptamer cTni6 against hcTnI. FIG. 4A is a curve of binding affinity for the third aptamer F17a against fibrinogen, FIG. 4B is a curve of binding affinity for the third aptamer F13a against fibrinogen, and FIG. 4C is a curve of binding affinity for the third aptamer F37a against fibrinogen. In addition, after binding the first aptamer N21a to NT-proBNP, the binding affinity of the first aptamer N21a is also measured by the surface plasmon resonance, and the binding affinity curve is obtained by plotting relative units (RU) of the first aptamer N21a with the concentration of NT-proBNP. Please refer to FIG. 2C, which is a curve of binding affinity for the first aptamer N21a against NT-proBNP.

In FIG. 2A, the first aptamer N10 has also a high affinity with NT-proBNP, and the corresponding Kd value of the first aptamer N10 is 19.8 nM for NT-proBNP. In FIG. 2B, the first aptamer N15 has a high affinity with NT-proBNP, and the corresponding Kd value for the first aptamer N15 is 59.6 nM for NT-proBNP. In FIG. 2C, the first aptamer N21a has a high affinity with NT-proBNP, and the corresponding Kd value of the first aptamer N21a is 62.84 nM for NT-proBNP. In FIG. 3A, the second aptamer cTni3 has a high affinity with hcTnI, and the corresponding Kd value of the second aptamer cTni3 is 2.3 nM for hcTnI. In FIG. 3B, the second aptamer cTni6 has also a high affinity with hcTnI, and the corresponding Kd value of the second aptamer cTni6 is 49.4 nM for hcTnI. In FIG. 4A, the third aptamer F17a has a high affinity with fibrinogen, and the corresponding Kd value of the third aptamer F17a is 59.0 nM for fibrinogen. In FIG. 4B, the third aptamer F13a has also a high affinity with fibrinogen, and the corresponding Kd value of the third aptamer F13a is 300.8 nM for fibrinogen. In FIG. 4C, the third aptamer F37a has also a high affinity with fibrinogen, and the corresponding Kd value of the third aptamer F37a is 95.0 nM for fibrinogen.

The results indicate that the binding affinities of the first aptamer, the second aptamer and the third aptamer of the present disclosure are in the nM range, which is already comparable to the range of antibody binding affinities.

1.2. Specificity Test

In the specificity test, the single-stranded DNA of the first aptamer, the second aptamer and the third aptamer are synthesized first. The magnetic beads coated with the target protein or the non-target protein are mixed with the first aptamer, the second aptamer or the third aptamer, and then the magnetic beads are captured by the magnet and the aptamers which are not bound to the magnetic beads are washed away. Then, the magnetic beads are heated to denature the proteins on the magnetic beads for releasing the bound aptamers into the supernatant. Quantitative PCR is performed using the supernatant to analyze the number of residual aptamers, and compared with each other to test the specificity of the first aptamer, the second aptamer, and the third aptamer. In theory, a specific aptamer should only bind to its corresponding target protein, but not to a non-corresponding protein. The aptamers tested in the example are the first aptamer N20a, the second aptamer Tn2, and the third aptamer F03s.

Figure 5A:
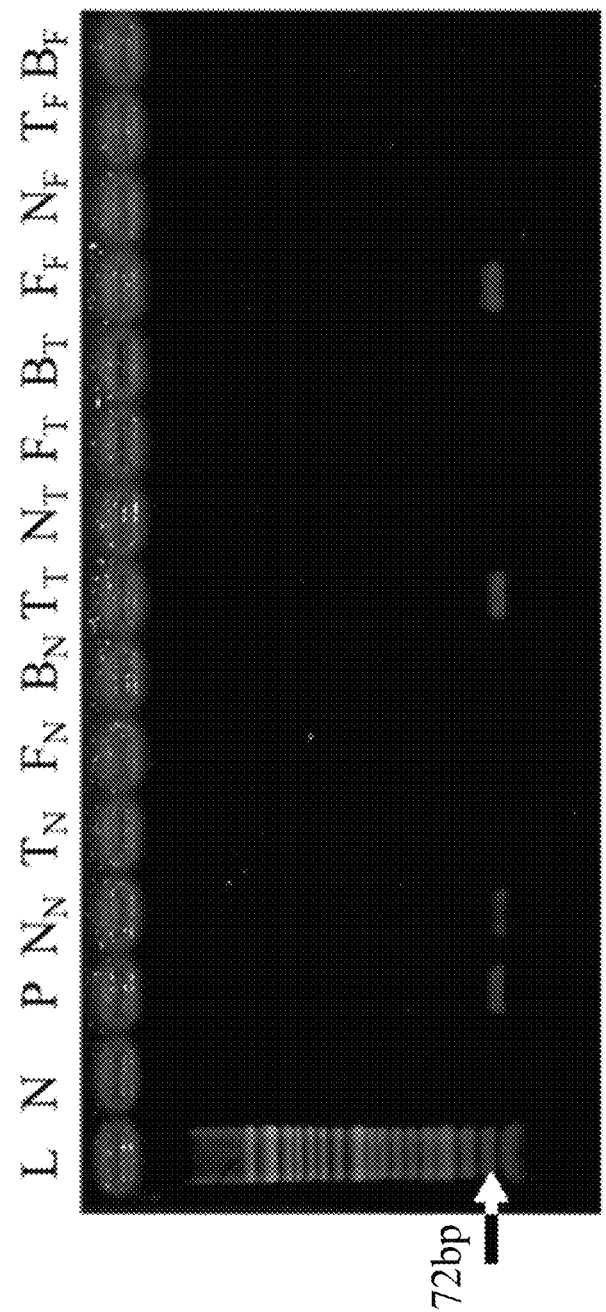
FIGS. 5A, 5B, 5C and 5D show specificity analysis results of a test kit for detecting a concentration of a cardiovascular disease-related biomarker according to one embodiment of the present disclosure.
Figure 5B:
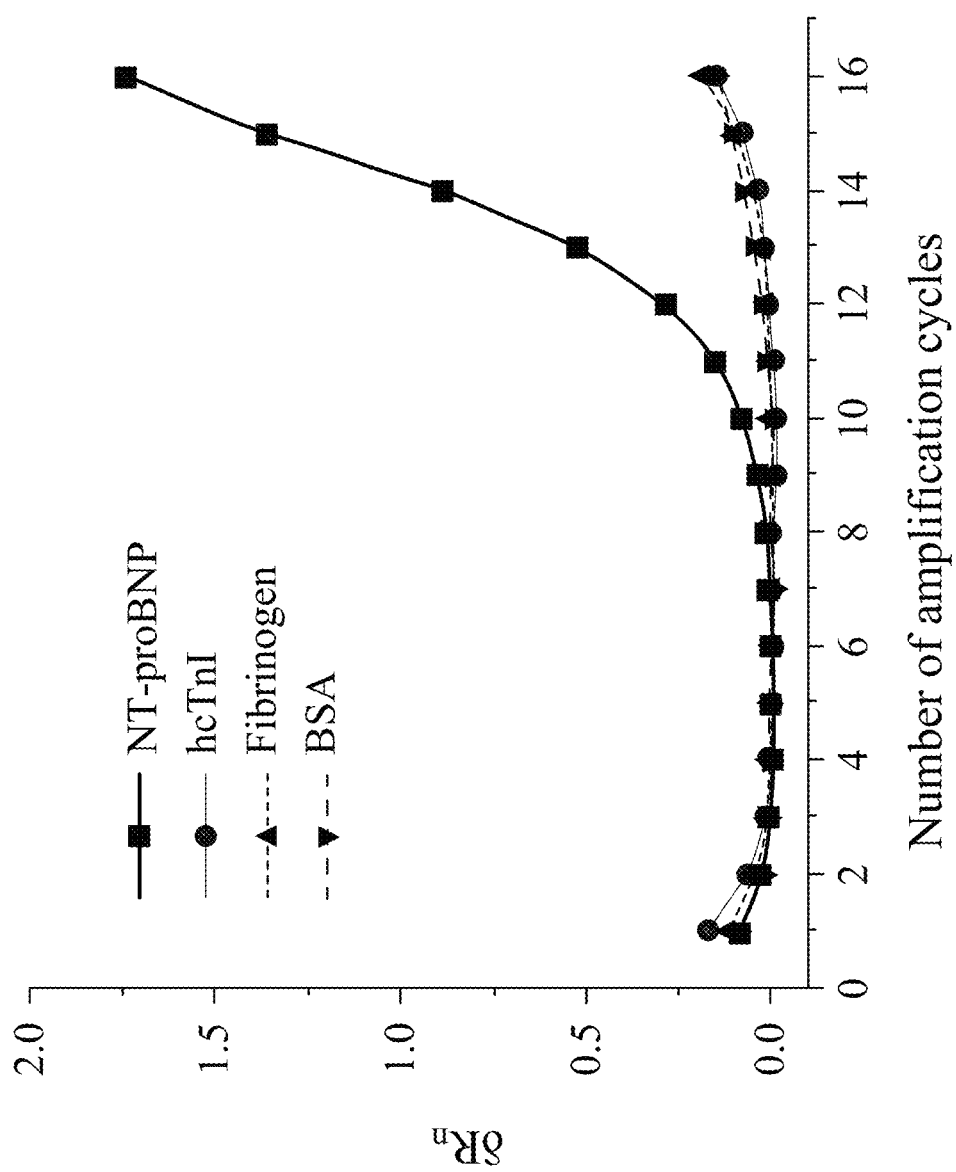
Figure 5C:
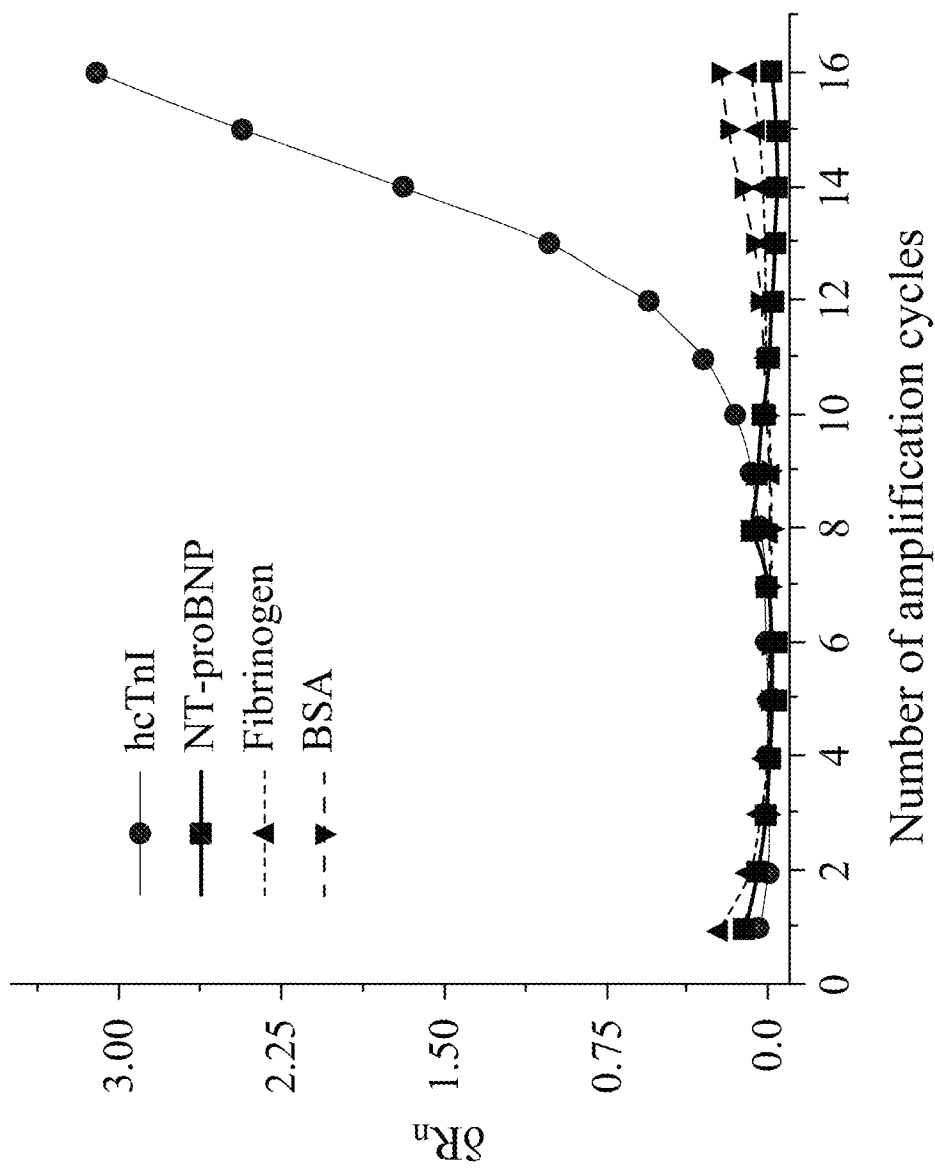
Figure 5D:
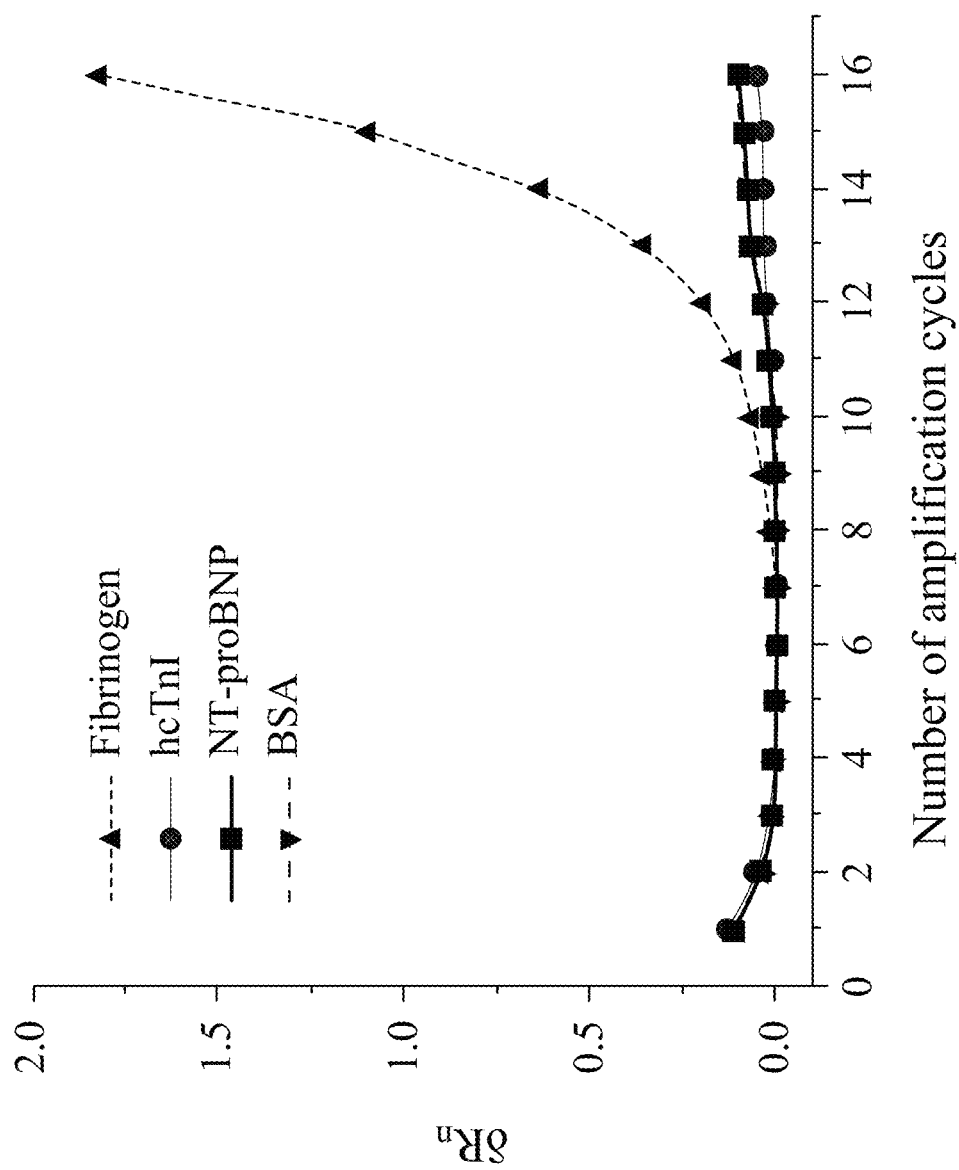

Please refer to FIGS. 5A, 5B, 5C and 5D, which show specificity analysis results of a test kit for detecting the concentration of the cardiovascular disease-related biomarker according to one embodiment of the present disclosure. FIG. 5A shows the gel electrophoresis result of each test group after quantitative PCR, wherein L represents ladder, N represents negative control, P represents positive control, $N_N$ represents the NT-proBNP with the first aptamer N20a, $T_N$ represents the hcTnI with the first aptamer N20a, $F_N$ represents the fibrinogen with the first aptamer N20a, and $B_N$ represents BSA protein with the first aptamer N20a. $T_T$ represents the hcTnI with the second aptamer Tn2, $N_T$ represents the NT-proBNP protein with the second aptamer Tn2, $F_T$ represents the fibrinogen protein with the second aptamer Tn2, and $B_T$ represents the BSA protein with the second aptamer Tn2. $F_F$ represents the fibrinogen protein with the third aptamer F03s, $N_F$ represents the NT-proBNP with the third aptamer F03s, $T_F$ represents the hcTnI with the third aptamer F03s, and $B_F$ represents the BSA protein with the third aptamer F03s. FIG. 5B shows quantitative PCR analysis results of the specificity binding and non-specificity binding of the first aptamer N20a. FIG. 5C shows quantitative PCR analysis results of the specificity binding and non-specificity binding of the second aptamer Tn2. FIG. 5D shows quantitative PCR analysis results of the specificity binding and non-specificity binding of the third aptamer F03s.

In FIG. 5A, an amplified DNA fragment detected at 72 bp indicates that there is still a single-stranded DNA residue after washing the mixed sample, indicating a strong affinity between the target protein and the aptamer. Please refer to FIGS. 5A and 5B. In FIG. 5A, when the aptamer is the first aptamer N20a, an amplified DNA fragment only can be detected in the group mixed with the magnetic beads coated with the NT-proBNP. The results of FIG. 5B also show that the first aptamer N20a only binds to the magnetic bead coated with the NT-proBNP. The results indicate that the first aptamer N20a only has a strong binding affinity with the NT-proBNP, but does not have binding affinities with the hcTnI and the fibrinogen. Please refer to FIGS. 5A and 5C. In FIG. 5A, when the aptamer is the second aptamer Tn2, an amplified DNA fragment only can be detected in the group mixed with the magnetic beads coated with the hcTnI. The results of FIG. 5C also show that the second aptamer Tn2 only binds to the magnetic bead coated with the hcTnI. The results indicate that the second aptamer Tn2 only has a strong binding affinity with the hcTnI, but does not have binding affinities with the NT-proBNP and the fibrinogen. Please refer to FIGS. 5A and 5D. In FIG. 5A, when the aptamer is the third aptamer F03s, an amplified DNA fragment only can be detected in the group mixed with the magnetic beads coated with the fibrinogen. The results of FIG. 5D also show that the third aptamer F03s only binds to the magnetic bead coated with the fibrinogen. The results indicate that the third aptamer F03s only has a strong binding affinity with the fibrinogen, but does not have binding affinity with the NT-proBNP and the hcTnI.

The results indicate that the first aptamer, the second aptamer and the third aptamer contained in the test kit for detecting the concentration of the cardiovascular disease-related biomarker of the present disclosure have good specificity for the corresponding target protein, but do not have specific binding for non-target proteins in BSA or other cardiovascular disease-related biomarkers.

II. The Concentration Detection Method of the Present Disclosure

The concentration detection method of the present disclosure is for in vitro detecting the concentration of the cardiovascular disease-related biomarker in the sample, and the test kit for detecting the concentration of the cardiovascular disease-related biomarker according to the present disclosure can be used. After mixing the sample with the test kit for detecting the concentration of the cardiovascular disease-related biomarker of the present disclosure, a binding value of the sample and the test kit for detecting the concentration of the cardiovascular disease-related biomarker is measured, and the binding value is brought into the regression equation established in advance to obtain the concentration of the cardiovascular disease-related biomarker in the sample.

Figure 6A:
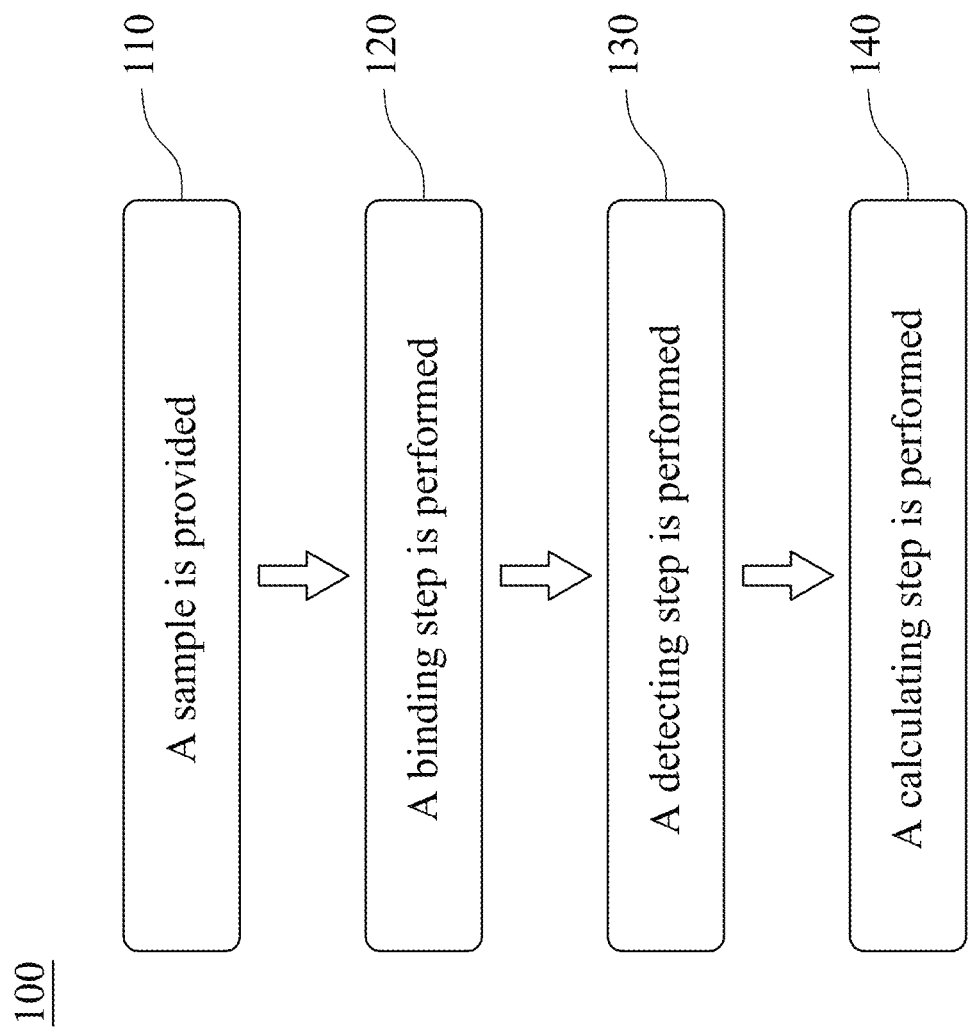
FIG. 6A is a flow diagram showing a concentration detection method according to another embodiment of the present disclosure.

Please refer to FIG. 6A, which is a flow diagram showing a concentration detection method 100 according to another embodiment of the present disclosure. In FIG. 6A, the concentration detection method 100 includes step 110, step 120, step 130 and step 140. The concentration detection method 100 is for detecting the concentration of the cardiovascular disease-related biomarker in the sample. The cardiovascular disease-related biomarker can be the NT-proBNP, the cTnI and/or the fibrinogen.

In step 110, the sample is provided. The sample is taken from a subject, and the sample can be blood, plasma or serum.

In step 120, a binding step is performed, wherein the binding step is for mixing the sample with the test kit for detecting the concentration of the cardiovascular disease-related biomarker of the present disclosure, and performing a binding reaction. The test kit for detecting the concentration of the cardiovascular disease-related biomarker of the present disclosure includes a group selected from the group consisting of the first aptamer, the second aptamer and the third aptamer. Further, the first aptamer can be bound to the first detectable label, and the first detectable label can be selected from the group consisting of the radioisotope, the enzyme, the fluorescent tag, the chemiluminescent tag, and the magnetic substance. The second aptamer can be bound to the second detectable label, and the second detectable label can be selected from the group consisting of the radioisotope, the enzyme, the fluorescent tag, the chemiluminescent tag, and the magnetic substance. The third aptamer can be bound to the third detectable label, and the third detectable label can be selected from the group consisting of the radioisotope, the enzyme, the fluorescent tag, the chemiluminescent tag, and the magnetic substance.

In step 130, a detecting step is performed, wherein the detecting step is for measuring a binding value of the sample by the test kit for detecting the concentration of the cardiovascular disease-related biomarker of the present disclosure. In detail, when the cardiovascular disease-related biomarker is the NT-proBNP, a first binding value of the sample with the first aptamer is measured in the detecting step. When the cardiovascular disease-related biomarker is the cTnI, a second binding value of the sample with the second aptamer is measured in the detecting step. When the cardiovascular disease-related biomarker is the fibrinogen, a third binding value of the sample with the third aptamer is measured in the detecting step.

In step 140, a calculating step is performed for bringing the binding value into the regression equation established in advance to obtain the concentration of the cardiovascular disease-related biomarker in the sample. In detail, the first binding value is brought into a first regression equation established in advance to obtain a concentration of the NT-proBNP in the calculating step, the second binding value is brought into a second regression equation established in advance to obtain a concentration of the cTnI in the calculating step, and the third binding value is brought into a third regression equation established in advance to obtain a concentration of the fibrinogen in the calculating step.

Figure 6B:
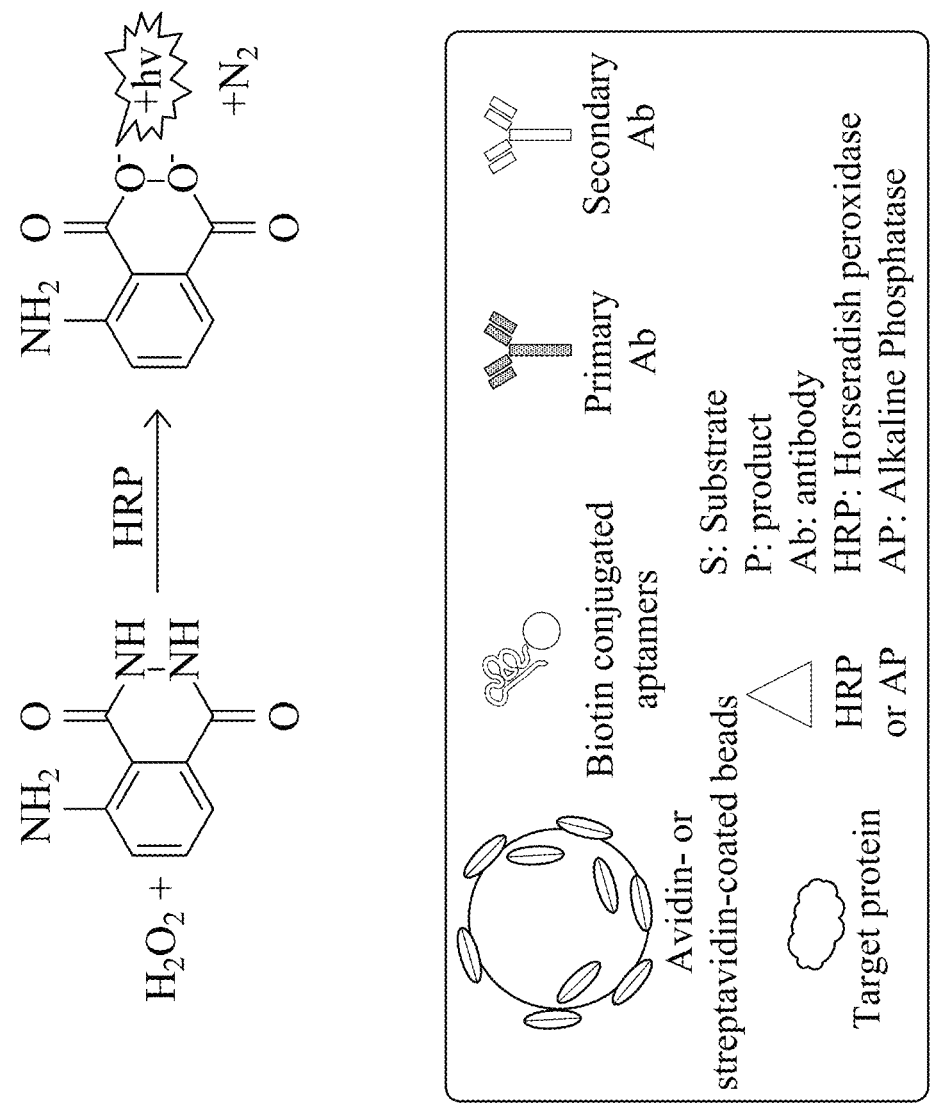
FIG. 6B is a schematic view the of the test kit for detecting the concentration of the cardiovascular disease-related biomarker according to Example 1 of the present disclosure.
Figure 6B:
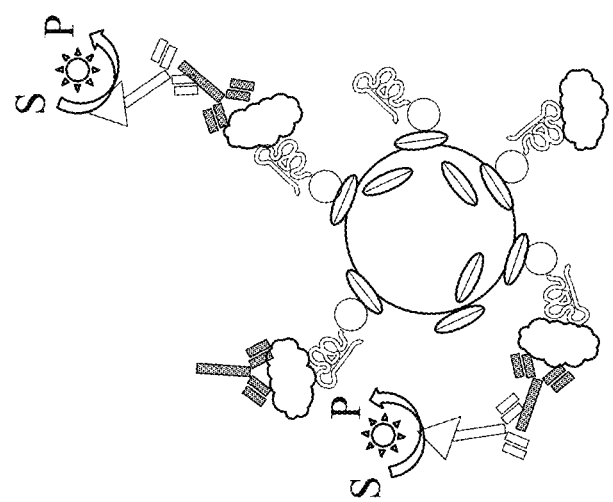
Figure 6C:
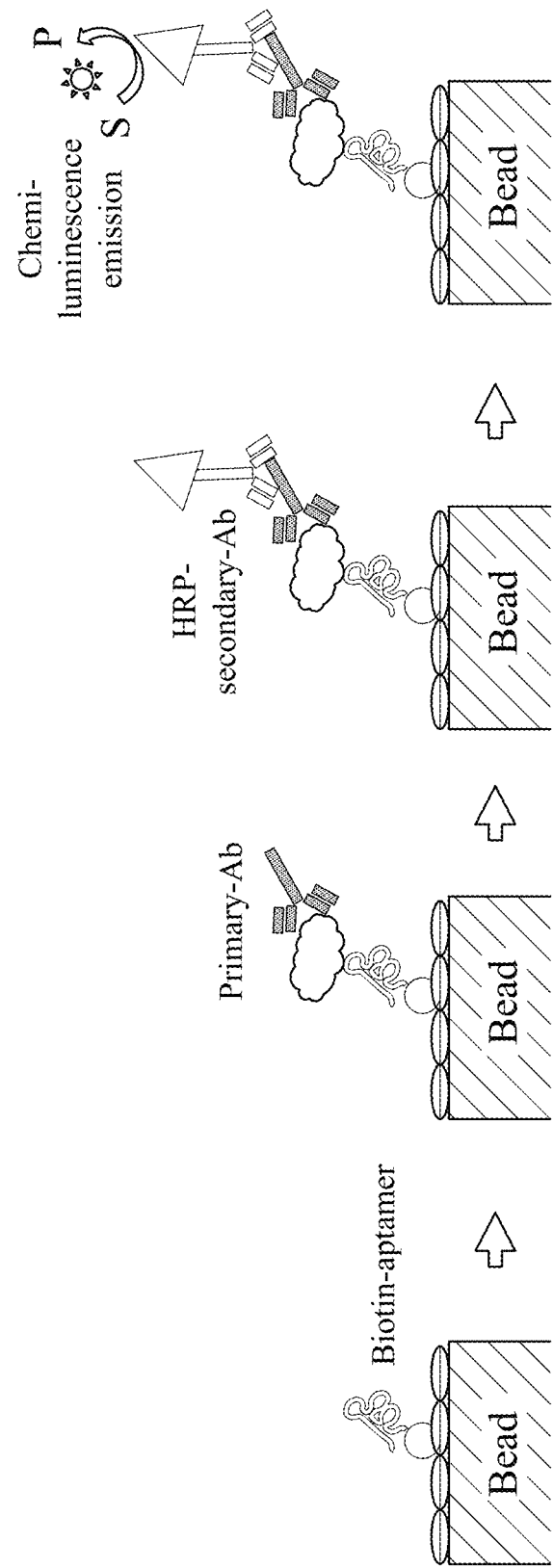
FIG. 6C is a schematic flow diagram showing the steps of performing concentration detection using the test kit for detecting the concentration of the cardiovascular disease-related biomarker according to Example 1 of the present disclosure.

For example, the cardiovascular disease-related biomarker to be tested is the cTnI. Please refer to FIGS. 6B and 6C, FIG. 6B is a schematic view the of the test kit for detecting the concentration of the cardiovascular disease-related biomarker according to Example 1 of the present disclosure, and FIG. 6C is a schematic flow diagram showing the steps of performing concentration detection using the test kit for detecting the concentration of the cardiovascular disease-related biomarker according to Example 1 of the present disclosure. The test kit for detecting the concentration of the cardiovascular disease-related biomarker of Example 1 is a second aptamer magnetic bead formed by binding a biotin-conjugated second aptamer to an avidin- or streptavidin-coated magnetic bead. After mixing the second aptamer coated magnetic bead with the sample, the proteins not bound to the second aptamer coated magnetic beads are washed away with the buffer solution. Then, the second aptamer coated magnetic beads and the sample mixtures are incubated with the primary anti-cTnI antibodies for a period of time. And then the primary anti-cTnI antibodies which are not bound to the second aptamer coated magnetic beads are washed away with the buffer solution. The second aptamer coated magnetic beads bound to the primary anti-cTnI antibody are incubated with secondary antibodies which are conjugated with horseradish peroxidase (HRP) or alkaline phosphatase (AP). After some time, the secondary antibodies that are not specifically bound to the primary antibody are washed away with the buffer solution, and then the substrates for luminescence are added. The second binding value of the sample with the second aptamer is measured by detecting the signal of luminescence, and the second binding value changes with the change of the concentration of the cTnI. Before assaying the samples with unknown concentrations, a second regression equation is established by measuring the serially diluted cTnI with known concentration mixed with the second aptamer coated magnetic bead. The signal values versus cTnI concentrations are plotted to acquire the second regression equation. When the sample with unknown concentration is subsequently detected, the measured signal value can be brought into the second regression equation to obtain the concentration of the cTnI.

Figure 7A:
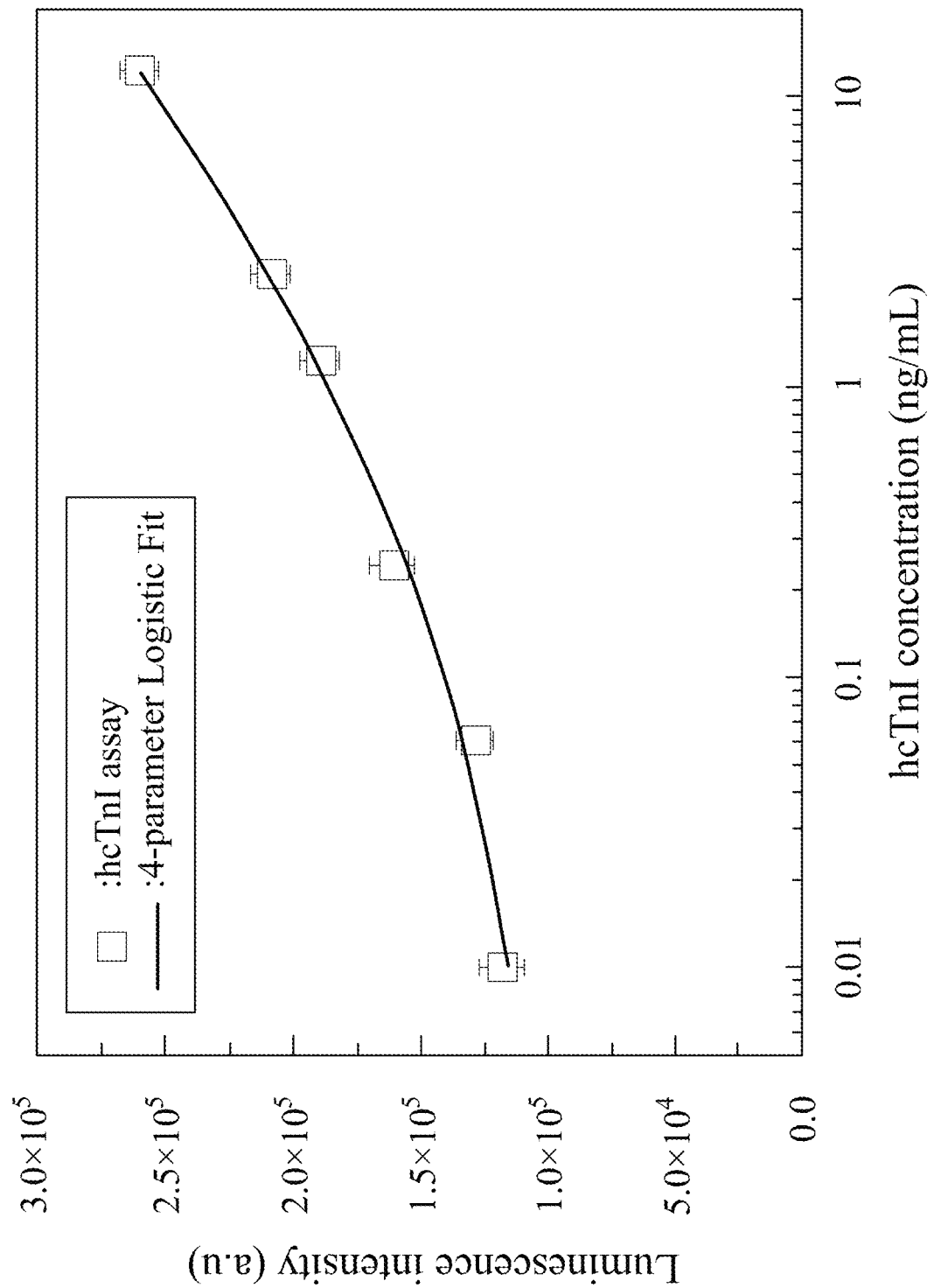
FIG. 7A shows analytical results of detecting purified cardiac Troponin I by the test kit for detecting the concentration of the cardiovascular disease-related biomarker according to Example 1 of the present disclosure.
Figure 7B:
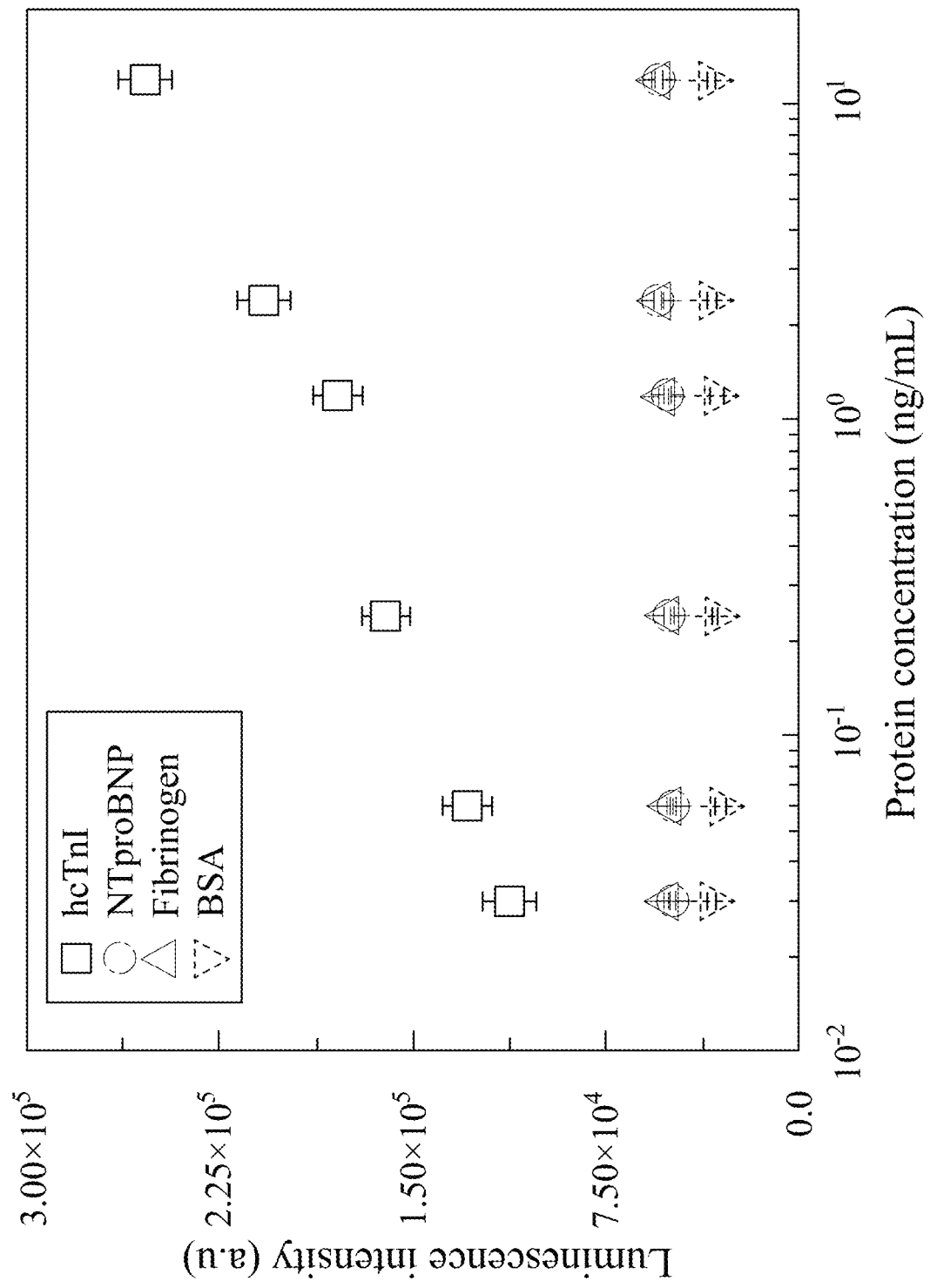
FIG. 7B shows specificity analytical results of the test kit for detecting the concentration of the cardiovascular disease-related biomarker according to Example 1 of the present disclosure.
Figure 7C:
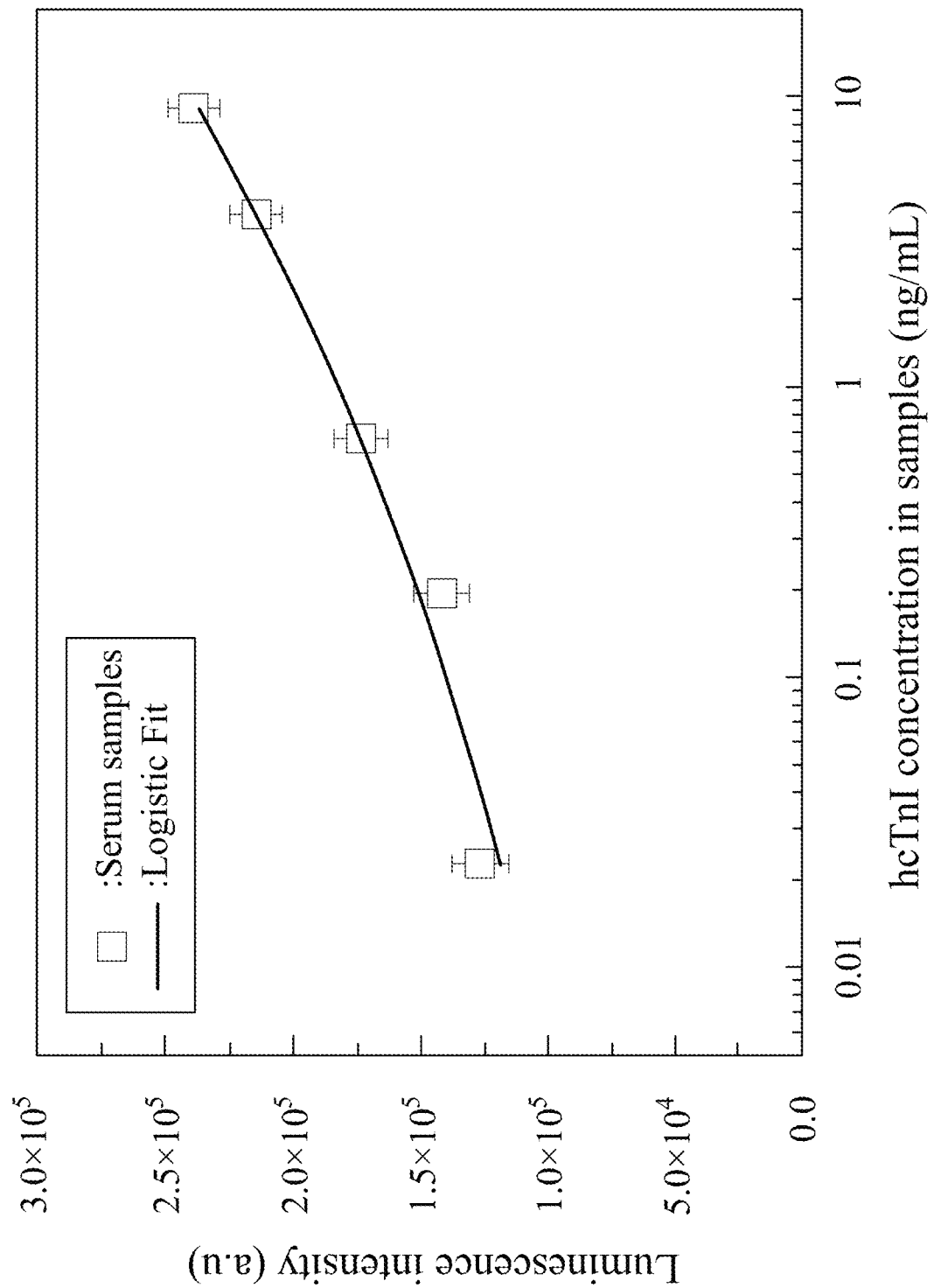
FIG. 7C shows analytical results of detecting serum samples by the test kit for detecting the concentration of the cardiovascular disease-related biomarker according to Example 1 of the present disclosure.

Please refer to FIGS. 7A, 7B and 7C, FIG. 7A shows analytical results of detecting purified cardiac Troponin I by the test kit for detecting the concentration of the cardiovascular disease-related biomarker according to Example 1 of the present disclosure. FIG. 7B shows specificity analytical results of the test kit for detecting the concentration of the cardiovascular disease-related biomarker according to Example 1 of the present disclosure. And FIG. 7C shows analytical results of detecting serum samples by the test kit for detecting the concentration of the cardiovascular disease-related biomarker according to Example 1 of the present disclosure.

In the experiment, the purified cTnI is diluted to 12 ng/mL, 2.4 ng/mL, 1.2 ng/mL, 0.24 ng/mL, 0.06 ng/mL, and 0.01 ng/mL, respectively. Then, 6 concentrations of the cTnI are separately mixed with the second aptamer coated magnetic beads, and the second binding value is measured by the method mentioned above. The relationship between the second binding value and the concentration is fitted by a 4-parameter logistic regression using the second binding values obtained at six different concentrations. The formula is $y=(A_1-A_2)/(1+(x/x_0)^p)+A_2$, where y represents the second binding value (that is the luminescence intensity in Example 1), x represents the concentration, and $A_1$ represents the initial binding value, $A_2$ represents the final binding value, $x_0$ represents the binding value turning point concentration, and p represents the power value. $A_1$, $A_2$, $x_0$ and p are the values obtained by curve fitting using the software, and the parameters obtained by fitting are fed back the regression equation to accomplish the formula that conforms to the standard concentration calibration curve. In FIG. 7A, the second aptamer coated magnetic beads used in the test kit show a good regression curve relationship with different concentrations of the cTnI, and the second aptamer coated magnetic beads can be subsequently used to detect the concentration of cTnI in the sample.

In addition, the cTnI, the NT-proBNP, the fibrinogen and BSA are separately diluted to 12 ng/mL, 2.4 ng/mL, 1.2 ng/mL, 0.24 ng/mL, 0.06 ng/mL and 0.01 ng/mL. Six concentrations of the cTnI, the NT-proBNP, the fibrinogen and BSA are separately mixed with the second aptamer coated magnetic beads, and the binding value is measured by the previously described method, respectively. In FIG. 7B, luminescence intensity can be detected only when the sample is the cTnI. When the sample is NT-proBNP, fibrinogen, or BSA, the luminescence signal value shows no dependence upon protein concentrations. The results indicate that the test kit for detecting the concentration of the cardiovascular disease-related biomarker of Example 1 has acceptable specificity towards target biomarkers.

Furthermore, serum samples with known cTnI concentration are separately mixed with the second aptamer coated magnetic beads, and the second binding values are measured by the method described before. In FIG. 7C, the assay shows a good curve distribution relationship with the different concentrations of the cTnI in the serum samples. Therefore, the test kit for detecting the concentration of the cardiovascular disease-related biomarker of the present disclosure can be used to detect the concentration of the cTnI in the serum samples.

To sum up, the test kit for detecting the concentration of the cardiovascular disease-related biomarker and the concentration detection method thereof are provided in the present disclosure. The test kit for detecting the concentration of the cardiovascular disease-related biomarker includes the first aptamer, the second aptamer and the third aptamer having binding affinity and specificity for cardiovascular disease-related biomarkers such as the NT-proBNP, the cTnI and/or the fibrinogen. The test kit for detecting the concentration of the cardiovascular disease-related biomarker can detect the concentration of the NT-proBNP, the cTnI and/or the fibrinogen in the sample, and then to evaluate whether the test subject has the risk of cardiovascular disease. The first aptamer, the second aptamer, and the third aptamer included in the test kit for detecting the concentration of the cardiovascular disease-related biomarker of the present disclosure are single-stranded DNA aptamers. Compared with currently widely used antibodies, the first aptamer, the second aptamer, and the third aptamer have advantages of lower production cost, a wider range of conditions on storage temperature, and fewer differences in production batches. Besides, the first aptamer, the second aptamer and the third aptamer can be used to develop new detection methods and new detection reagents, and can also be applied to develop semiconductor, electrochemical or other types of biosensors. These new types of biosensor, by combining with these microfluidic devices may extend out to produce micro-detection chips or assay kits. Furthermore, the test kit for detecting the concentration of the cardiovascular disease-related biomarker of the present disclosure includes at least one single-stranded DNA aptamer screened for three cardiovascular disease-related biomarkers, and can be combined with a micro-detection chip or test kit for measuring the concentrations of different cardiovascular disease-related biomarkers at once. Therefore, may to achieve better assess the risk of cardiovascular disease for the test subject. Accordingly, such miniaturized test instruments or kits can help in achieving the goal of Point-of-Care.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A test kit for detecting a concentration of a cardiovascular disease-related biomarker, comprising:
   a group selected from the group consisting of a first aptamer, a second aptamer and a third aptamer;
   wherein the first aptamer has binding specificity to a N-terminal pro-brain natriuretic peptide (NT-proBNP) and comprises a nucleotide sequence of SEQ ID NO: 1, the second aptamer has binding specificity to a cardiac Troponin I (cTnI) and comprises a nucleotide sequence of SEQ ID NO: 2, and the third aptamer has binding specificity to a fibrinogen and comprises a nucleotide sequence of SEQ ID NO: 3.

2. The test kit of claim 1, wherein the first aptamer further comprises a group selected from a nucleotide sequence of SEQ ID NO: 4, a nucleotide sequence of SEQ ID NO: 5, and a nucleotide sequence of SEQ ID NO: 6.

3. The test kit of claim 1, wherein the second aptamer further comprises a group selected from a nucleotide sequence of SEQ ID NO: 7 and a nucleotide sequence of SEQ ID NO: 8.

4. The test kit of claim 1, wherein the third aptamer further comprises a group selected from a nucleotide sequence of SEQ ID NO: 9, a nucleotide sequence of SEQ ID NO: 10, and a nucleotide sequence of SEQ ID NO: 11.

5. The test kit of claim 1, further comprising a first detectable label on the first aptamer, wherein the first detectable label is selected from the group consisting of a radioisotope, an enzyme, a fluorescent tag, a chemiluminescent tag, and a magnetic substance.

6. The test kit of claim 1, further comprising a second detectable label on the second aptamer, wherein the second detectable label is selected from the group consisting of a radioisotope, an enzyme, a fluorescent tag, a chemiluminescent tag, and a magnetic substance.

7. The test kit of claim 1, further comprising a third detectable label on the third aptamer, wherein the third detectable label is selected from the group consisting of a radioisotope, an enzyme, a fluorescent tag, a chemiluminescent tag, and a magnetic substance.

8. A concentration detection method for detecting a concentration of a cardiovascular disease-related biomarker in a sample, the concentration detection method comprising:
   providing the sample;
   performing a binding step, wherein the binding step is for mixing the sample with the test kit for detecting the concentration of the cardiovascular disease-related biomarker of claim 1 and performing a binding reaction;
   performing a detecting step, wherein the detecting step is for measuring a binding value of the sample and the test kit for detecting the concentration of the cardiovascular disease-related biomarker; and
   performing a calculating step, wherein the calculating step is for bringing the binding value into a regression equation established in advance to obtain the concentration of the cardiovascular disease-related biomarker in the sample.

9. The concentration detection method of the claim 8, wherein the cardiovascular disease-related biomarker is an N-terminal pro-brain natriuretic peptide (NT-proBNP), a cardiac Troponin I (cTnI) or a fibrinogen.

10. The concentration detection method of the claim 9, wherein when the cardiovascular disease-related biomarker is the N-terminal pro-brain natriuretic peptide, a first binding value of the sample with the first aptamer is measured in the detecting step, and the first binding value is brought into a first regression equation established in advance to obtain a concentration of the N-terminal pro-brain natriuretic peptide in the calculating step.

11. The concentration detection method of the claim 9, wherein when the cardiovascular disease-related biomarker is the cardiac Troponin I, a second binding value of the sample with the second aptamer is measured in the detecting step, and the second binding value is brought into a second regression equation established in advance to obtain a concentration of the cardiac Troponin I in the calculating step.

12. The concentration detection method of the claim 9, wherein when the cardiovascular disease-related biomarker is the fibrinogen, a third binding value of the sample with the third aptamer is measured in the detecting step, and the third binding value is brought into a third regression equation established in advance to obtain a concentration of the fibrinogen in the calculating step.

* * * * *

SEQUENCE LISTING

```
<160> NUMBER OF SEQ ID NOS: 11

<210> SEQ ID NO 1
<211> LENGTH: 72
<212> TYPE: DNA
<213> ORGANISM: Artificial Sequence
<220> FEATURE:
<223> OTHER INFORMATION: N20a

<400> SEQUENCE: 1
ggcaggaaga caaacaggtc gtagtggaaa ctgtccaccg tagaccggtt atctagtggt      60
ctgtggtgct gt                                                         72

<210> SEQ ID NO 2
<211> LENGTH: 72
<212> TYPE: DNA
<213> ORGANISM: Artificial Sequence
<220> FEATURE:
<223> OTHER INFORMATION: Tn2

<400> SEQUENCE: 2
ggcaggaaga caaacaccca accgaggatg caacgcttgt tgtcatactg tgatgttggt      60
ctgtggtgct gt                                                         72

<210> SEQ ID NO 3
<211> LENGTH: 72
<212> TYPE: DNA
<213> ORGANISM: Artificial Sequence
<220> FEATURE:
<223> OTHER INFORMATION: F03s
```

-continued

<400> SEQUENCE: 3
ggcaggaaga caaacagcac cgggtccgaa acaggcttag gtatgatcac agctcatggt    60
ctgtggtgct gt                                                       72

<210> SEQ ID NO 4
<211> LENGTH: 72
<212> TYPE: DNA
<213> ORGANISM: Artificial Sequence
<220> FEATURE:
<223> OTHER INFORMATION: N10

<400> SEQUENCE: 4
ggcaggaaga caaacatgta aatccagcgg ggttgatccc cctgtcgtcc tatgtgtggt    60
ctgtggtgct gt                                                       72

<210> SEQ ID NO 5
<211> LENGTH: 72
<212> TYPE: DNA
<213> ORGANISM: Artificial Sequence
<220> FEATURE:
<223> OTHER INFORMATION: N15

<400> SEQUENCE: 5
ggcaggaaga caaacaacac gcagttgctt tctactcgtc gggcctcctg ttagcatggt    60
ctgtggtgct gt                                                       72

<210> SEQ ID NO 6
<211> LENGTH: 72
<212> TYPE: DNA
<213> ORGANISM: Artificial Sequence
<220> FEATURE:
<223> OTHER INFORMATION: N21a

<400> SEQUENCE: 6
ggcaggaaga caaacacgca tagcgaggaa gtgttgtgtg tggtggaagc ctagcatggt    60
ctgtggtgct gt                                                       72

<210> SEQ ID NO 7
<211> LENGTH: 72
<212> TYPE: DNA
<213> ORGANISM: Artificial Sequence
<220> FEATURE:
<223> OTHER INFORMATION: cTni3

<400> SEQUENCE: 7
ggcaggaaga caaacagggg tacttagcat aggagttttg ttctgtcgca cctcgttggt    60
ctgtggtgct gt                                                       72

<210> SEQ ID NO 8
<211> LENGTH: 72
<212> TYPE: DNA
<213> ORGANISM: Artificial Sequence
<220> FEATURE:
<223> OTHER INFORMATION: cTni6

<400> SEQUENCE: 8
ggcaggaaga caaacacggg gcggccgaaa caatgcgttt cggacccagc aactcgtggt    60
ctgtggtgct gt                                                       72

<210> SEQ ID NO 9

```
<211> LENGTH: 72
<212> TYPE: DNA
<213> ORGANISM: Artificial Sequence
<220> FEATURE:
<223> OTHER INFORMATION: F17a

<400> SEQUENCE: 9
ggcaggaaga caaacaccac gatgagtgtt cttcgtaccg tcgacagcgg ctggtttggt      60
ctgtggtgct gt                                                         72

<210> SEQ ID NO 10
<211> LENGTH: 72
<212> TYPE: DNA
<213> ORGANISM: Artificial Sequence
<220> FEATURE:
<223> OTHER INFORMATION: F13a

<400> SEQUENCE: 10
ggcaggaaga caaacacaca gggataacta gatgactagg tgtccccggt tcctactggt      60
ctgtggtgct gt                                                         72

<210> SEQ ID NO 11
<211> LENGTH: 72
<212> TYPE: DNA
<213> ORGANISM: Artificial Sequence
<220> FEATURE:
<223> OTHER INFORMATION: F37a

<400> SEQUENCE: 11
ggcaggaaga caaacaggac cgcttcgtcc aggtgacatc gagacccgca attgtatggt      60
ctgtggtgct gt                                                         72
```